United States Patent
Honjo et al.

(10) Patent No.: US 9,073,994 B2
(45) Date of Patent: *Jul. 7, 2015

(54) IMMUNOPOTENTIATIVE COMPOSITION

(71) Applicants: Ono Pharmaceutical Co., LTD., Osaka (JP); Tasuku Honjo, Kyoto (JP)

(72) Inventors: Tasuku Honjo, Kyoto (JP); Nagahiro Minato, Kyoto (JP); Yoshiko Iwai, New York, NY (US); Shiro Shibayama, Tsukuba (JP)

(73) Assignees: Ono Pharmaceutical Co., LTD. (JP); Tasuku Honjo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/550,585

(22) Filed: Nov. 21, 2014

(65) Prior Publication Data

US 2015/0093380 A1    Apr. 2, 2015

Related U.S. Application Data

(62) Division of application No. 14/245,692, filed on Apr. 4, 2014, which is a division of application No. 12/959,307, filed on Dec. 2, 2010, now Pat. No. 8,728,474, which is a division of application No. 12/538,698, filed on Aug. 10, 2009, now Pat. No. 8,168,179, which is a division of application No. 10/519,925, filed as application No. PCT/JP03/08420 on Jul. 2, 2003, now Pat. No. 7,595,048.

(30) Foreign Application Priority Data

Jul. 3, 2002  (JP) ................. 2002-194491
Feb. 6, 2003  (JP) ................. 2003-029846

(51) Int. Cl.
*C07K 16/28* (2006.01)
*A61K 39/395* (2006.01)
*A61K 31/7088* (2006.01)
*C12Q 1/02* (2006.01)
*G01N 33/50* (2006.01)
*G01N 33/574* (2006.01)
*A61K 38/21* (2006.01)
*C07K 16/18* (2006.01)
*A61K 9/00* (2006.01)
*A61K 45/06* (2006.01)
*A61K 47/26* (2006.01)
*A61K 39/00* (2006.01)

(52) U.S. Cl.
CPC ......... *C07K 16/2803* (2013.01); *A61K 31/7088* (2013.01); *A61K 2039/505* (2013.01); *C07K 16/2818* (2013.01); *C07K 16/2827* (2013.01); *C07K 2316/96* (2013.01); *C07K 2317/54* (2013.01); *C07K 2317/73* (2013.01); *C12Q 1/025* (2013.01); *G01N 33/5011* (2013.01); *G01N 33/574* (2013.01); *G01N 2500/00* (2013.01); *A61K 38/212* (2013.01); *A61K 39/3955* (2013.01); *C07K 16/18* (2013.01); *A61K 9/0019* (2013.01); *A61K 45/06* (2013.01); *A61K 47/26* (2013.01); *A61K 2039/507* (2013.01); *C07K 2317/21* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 5,324,514 A | 6/1994 | Sipos | |
| 5,629,204 A | 5/1997 | Honjo et al. | |
| 5,698,520 A | 12/1997 | Honjo et al. | |
| 5,897,862 A | 4/1999 | Hardy et al. | |
| 6,051,227 A | 4/2000 | Allison et al. | |
| 6,632,927 B2 | 10/2003 | Adair et al. | |
| 6,632,976 B1 | 10/2003 | Tomizuka et al. | |
| 6,803,192 B1 | 10/2004 | Chen | |
| 6,808,710 B1 | 10/2004 | Wood et al. | |
| 6,936,704 B1 | 8/2005 | Freeman et al. | |
| 7,029,674 B2 | 4/2006 | Carreno et al. | |
| 7,041,474 B2 | 5/2006 | Holtzmann et al. | |
| 7,101,550 B2 | 9/2006 | Wood et al. | |
| 7,105,328 B2 | 9/2006 | Wood et al. | |
| 7,122,372 B2 | 10/2006 | Hardy et al. | |

(Continued)

FOREIGN PATENT DOCUMENTS

| | | | |
|---|---|---|---|
| AU | 774391 B2 | 2/2001 | |
| EP | 0 670 369 A2 | 9/1995 | |

(Continued)

OTHER PUBLICATIONS

Notification of Reasons for Refusal, dated Jul. 14, 2009, issued by the Japanese Patent Office in Japanese Application No. 2004-519238.

(Continued)

*Primary Examiner* — Ilia Ouspenski
(74) *Attorney, Agent, or Firm* — Sterne, Kessler, Goldstein & Fox P.L.L.C.

(57) ABSTRACT

Compositions for cancer or infection treatment via immunopotentiation caused by inhibition of immunosuppressive signal induced by PD-1, PD-L1, or PD-L2 and therapies using them, immunopotentiative substrates included as the active ingredient, screening methods of the substrates for cancer or infection treatment, cell lines used for the screening methods, evaluation methods that selects the substrates for cancer treatment, and carcinoma cell transplanted mammals used for the evaluation methods.

The compositions of the present invention that inhibits the function of PD-1, PD-L1, or PD-L2 are useful for cancer or infection treatment.

30 Claims, 17 Drawing Sheets

(56) References Cited

U.S. PATENT DOCUMENTS

| | | |
|---|---|---|
| 7,329,639 B2 | 2/2008 | Hardy et al. |
| 7,332,582 B2 | 2/2008 | Hardy et al. |
| 7,423,128 B2 | 9/2008 | Gazit-Bornstein et al. |
| 7,488,802 B2 | 2/2009 | Collins et al. |
| 7,563,869 B2 | 7/2009 | Honjo et al. |
| 7,595,048 B2 * | 9/2009 | Honjo et al. ............... 424/142.1 |
| 7,794,710 B2 | 9/2010 | Chen et al. |
| 7,858,746 B2 | 12/2010 | Honjo et al. |
| 8,008,449 B2 | 8/2011 | Korman et al. |
| 8,168,179 B2 | 5/2012 | Honjo et al. |
| 8,728,474 B2 * | 5/2014 | Honjo et al. ............... 424/144.1 |
| 8,779,105 B2 | 7/2014 | Korman et al. |
| 2002/0164600 A1 | 11/2002 | Freeman et al. |
| 2003/0232323 A1 | 12/2003 | Freeman et al. |
| 2004/0073957 A1 | 4/2004 | Tomizuka et al. |
| 2004/0241745 A1 | 12/2004 | Honjo et al. |
| 2006/0110383 A1 | 5/2006 | Honjo et al. |
| 2007/0065427 A1 | 3/2007 | Freeman et al. |
| 2007/0202100 A1 | 8/2007 | Wood et al. |
| 2008/0025979 A1 | 1/2008 | Honjo et al. |
| 2011/0081341 A1 | 4/2011 | Honjo et al. |
| 2013/0133091 A1 | 5/2013 | Korman et al. |
| 2014/0212422 A1 | 7/2014 | Korman et al. |
| 2014/0294852 A1 | 10/2014 | Korman et al. |
| 2014/0314714 A1 | 10/2014 | Honjo et al. |
| 2014/0328833 A1 | 11/2014 | Korman et al. |
| 2014/0348743 A1 | 11/2014 | Korman |

FOREIGN PATENT DOCUMENTS

| | | |
|---|---|---|
| EP | 0742795 B1 | 11/1996 |
| EP | 1445264 A1 | 8/2004 |
| EP | 1537878 A1 | 6/2005 |
| EP | 1 591 527 A1 | 11/2005 |
| EP | 2206517 A1 | 7/2010 |
| EP | 2243493 A1 | 10/2010 |
| EP | 2161336 B1 | 7/2013 |
| JP | 7-291996 A | 11/1995 |
| JP | 2002194491 | 7/2002 |
| JP | 2003029846 | 2/2003 |
| JP | 2004512005 A | 4/2004 |
| WO | WO-9707671 A1 | 3/1997 |
| WO | WO 00/32231 A1 | 6/2000 |
| WO | WO 00/71078 A2 | 11/2000 |
| WO | WO 01/14557 A1 | 3/2001 |
| WO | WO-0114424 A2 | 3/2001 |
| WO | WO 02/00692 A2 | 1/2002 |
| WO | WO 02/00730 A2 | 1/2002 |
| WO | WO-02/32378 A2 | 4/2002 |
| WO | WO-02/34205 A2 | 5/2002 |
| WO | WO 02/078731 A1 | 10/2002 |
| WO | WO 02/079499 A1 | 10/2002 |
| WO | WO 02/086083 A2 | 10/2002 |
| WO | WO-03006636 A1 | 1/2003 |
| WO | WO 03/011911 A1 | 2/2003 |
| WO | WO-03033644 A2 | 4/2003 |
| WO | WO 03/042402 A2 | 5/2003 |
| WO | WO-03099196 A2 | 12/2003 |
| WO | WO-2004004771 A1 | 1/2004 |
| WO | WO 2004/056875 A1 | 7/2004 |
| WO | WO-2004072286 A1 | 8/2004 |
| WO | WO-2006021955 A2 | 3/2006 |
| WO | WO 2006/121168 A1 | 11/2006 |
| WO | WO-2006124269 A2 | 11/2006 |
| WO | WO-2007005874 A2 | 1/2007 |
| WO | WO-2013173223 A1 | 11/2013 |

OTHER PUBLICATIONS

Winslow, "New Cancer Drugs Harness Power of Immune System", Wall Street Journal, May 15, 2013, retrieved from http://online.wsj.com/newslarticles/SB10001424127887323398204578485401089823868 on Feb. 9, 2014; p. 1.

Pardoll, "The blockade of immune checkpoints in cancer immunotherapy," Nature Reviews Cancer, 2012, 12:252-264.

Zou et al., "Inhibitory B7-family molecules in the tumour microenvironment," Nature Reviews Immunology, 2008, 8:467-477.

Wong et al., "Programmed death-1 blockade enhances expansion and functional capacity of human melanoma antigen-specific CTLs," International Immunology, 2007, 19(10):1223-1234.

Weber et al., "Safety, Efficacy, and Biomarkers of Nivolumab With Vaccine in Ipilimumab-Refractory or-Naive Melanoma," Journal of Clinical Oncology, 2013, 31(34):4311-4318.

Creelan, "Update on Immune Checkpoint Inhibitors in Lung Cancer." Cancer Control, 2014, 21(1):80-89.

Antonia et al., "Association of tumor PD-L1 expression and immune biomarkers with clinical activity in patients with non-small cell lung cancer (NSCLC) treated with nivolumab," IASLC $15_{th}$ World Conference on Lung Cancer, Oct. 2013, retrieved from http://web.oncoletter.ch on Feb. 11, 2014.

Topalian et al., "Safety, Activity, and Immune Correlates of Anti-PD-1 Antibody in Cancer," The New England Journal of Medicine, 2012. 366(26):2443-2454.

Topalian, S ., "Q&A: Suzanne Topalian on Immune Therapies," Cancer Discovery, 2013, retrieved from cancerdiscovery.aacrjournals.org on Feb. 7, 2014; p. 712.

Collins et al., U.S. Appl. No. 60/435,354, filed Dec. 23, 2002, retrieved from http://portal.uspto.gov/pair/PublicPair on Mar. 4, 2014; pp. 1-91.

Communication from the Japanese Patent Office mailed Jul. 10, 2012, in Japanese application No. 2009-203514.

European Office Action issued Aug. 18, 2011, in corresponding European Patent Application No. 10172772.5 (in the name of Ono Pharmaceutical Co., Ltd.).

EP Application No. 03741154.3, Notice of Opposition dated Jul. 8, 2011, issued by the EPO in the name of Ono Pharmaceutical Co., Lto. et al.

"About the Internet Archive: General Information", Internet Archive, 2001, 10 pages, retrieved online from http://www.archive.ora/about/about.php on Apr. 5, 2011.

Affinity purified anti-mouse PD-1 (PD1): Archived website information for J43 and J116 antibodies; eBioscience and Waybackmachine/org 2002, accessed on Jun. 14, 2011, 4 pages, accessed from http://web.archive.org/web/20020301031217 and http://ebioscience/specs/antibody14/14-9985.

Agata, Y., et al., "Expression of the PD-1 antigen on the surface of stimulated mouse T and B lymphocytes," International Immunology 8(5):765-772, Oxford University Press, England (1996).

"Anti-Human CD 279 (PD-1) Functional Grade Purified: murine anti-PD-1 antibody J116", eBioscience, Information Sheet, 2000, 2 pages.

Bennett, F., et al., "Program death-1 engagement upon TCR activation has distinct effects on costimulation and cytokine-driven proliferation: attenuation of ICOS, IL-4, and IL-21, but not CD28, IL-15 responses," The Journal of Immunology 170(2):711-718, The American of Immunologists, United States (Jan. 2003).

Brown, J.A., et al., "Expression and functional consequences of PD-1 ligands on natural APCS and tumors," The FASEB Journal 15(4):A345(abstract No. 275.23), Federation of American Societies for Experimental Biology, United States (2001).

Response to the communication pursuant to Art. 96(2) for EP Application No. 03741154.3, mailed on Jun. 25, 2007, 7 pages.

EP Publication No. 1576014, Excerpt from Register of European Patents, retrieved online from https://register.epo.org/espacenet/application?number=EP03780521 accessed on May 27, 2011.

Freeman, G.J., et al., "Engagement of the PD-1 immunoinhibitory receptor by a novel B7 family member leads to negative regulation of lymphocyte activation," The Journal of Experimental Medicine 192(7)1027-1034, The Rockefeller University Press, United States (2000).

Freeman, G.J., et al., "Engagement of the PD-1 Immunoinhibitory Receptor by a Novel B7-Family Member Leads to Negative Regulation of Lymphocyte Activation," Blood 96(11): 810a-811a (Abstract No. 3502) (2000).

(56) References Cited

OTHER PUBLICATIONS

Iwai, Y., et al.,"Microanatomical localization of PD-1 in human tonsils," Immunology Letters 83(3):215-220, Elsevier, Netherlands (Oct. 2002).
Iwai, Y., et al., Online Publication of "Involvement of PD-L 1tumor cells in the escape from host immune system and tumor immunotherapy by PD-L1 blockade," Proceedings of the National Academy of Sciences United States of America 99(19): 12293-12297 (Sep. 2002), accessed at http://www.ncbi.nlm.nih.gov/pmc/articles/PMC129438/?report=abstract, accessed on Jun. 14, 2011.
Iwai, Y., et al., Online Publication of "Microanatomical localization of PD-1 in human tonsils," Immunology Letters 83(3):215-220, 1 page (Oct. 2002).
Latchman, Y.. et al., "PD-L2 is a second ligand for PD-1 and inhibits T cell activation," Nature Immunology 2(3):261-268, Nature Publishing Group, United States (2001).
Ozkaynak, E., et al.,"Programmed death-1 targeting can promote allograft survival," The Journal of Immunology 169(11):6546-6553, The American Association of Immunologists, United States (Dec. 2002).
Extended European Search Report for EP Application No. 10161767. 8, European Patent Office, Netherlands, mailed on Jun. 7, 2010.
Extended European Search Report for EP Application No. 10161767. 8, European Patent Office, Netherlands, mailed on Oct. 5, 2010.
Tamura, H., et al., "B7-H1 costimulation preferentially enhances CD28-independent T-helper cell function," Blood 97(6):1809-1816, The American Society of Hematology, United States (2001).
Dong, H., et al., "Tumor-associated B7-H1 promotes T-cell apoptosis: a potential mechanism of immune evasion," Nature Medicine 8(8):793-800, Nature Publishing Company, United States (Aug. 2002).
Nishimura, H., et al., "Immunological studies on PD-1 deficient mice: implication of PD-1 as a negative regulator for B cell responses," International Immunology 10(10):1563-1572, Oxford University Press, England (1998).
Yamazaki, T., et al.,"Expression of programmed death 1 ligands by murine T cells and APC," The Journal of Immunology 169(10):5538-5545, The American Association of Immunologists, United States (Nov. 2002).
Iwai, Y., et al., "Involvement of PD-L1 on tumor cells in the escape from host immune system and tumor immunotherapy by PD-L1 blockade," Proceedings of the National Academy of Sciences USA 99(19):12293-12297, The National Academy of Sciences of the United States (Sep. 2002).
Zuberek, K., "The role of in vivo PD-1/PD-L1 interactions in syngeneic and allogeneic antitumor responses in murine tumor models," Blood 98(11):42B (2001).
Supplementary Partial European Search Report for EP Application No. 03741154.3, European Patent Office, The Hague, mailed on Oct. 26, 2006.
Brown, J.A., et al., "Blockade of PD-1 ligands on dendritic cells enhances T cells activation and cytokine production," FASEB Journal 16(4):A710-517.4, Federation of American Societies for Experimental Biology, United States (Mar. 2002).
Brown, J.A., et al., "Blockade of programmed death-1 ligands on dendritic cells enhances T cell activation and cytokine production," The Journal of Immunology 170(3):1257-1266, The American Association of Immunologists, United States (Feb. 2003).
International Search Report for International Application No. PCT/JP03/08420, ISA/JP, Japan, mailed on Oct. 21, 2003 Brahmer.
Brahmer., "Safety and activity of MDX-1106 (ONO-4538) anti-PD-1 monoclonal antibody in patients with selected refractory or relapsed malignancies," Journal of Clinical Oncology 26:Abstract No. 3006, American Society of Clinical Oncology, United States (2008).
Huang, Z., "Structural chemistry and therapeutic intervention of protein-protein interactions in immune response, human immunodeficiency virus entry, and apoptosis," Pharmacology & Therapeutics 86(3):201-215, Pergamon Press, England (2000).

Blazar, B.R., et al., "Infusion of anti-B7.1 (CD80) and anti-B7.2 (CD86) monoclonal antibodies inhibits murine graft-versus-host disease lethality in part via direct effects on CD4+ and CD8+ T cells," The Journal of Immunology 157(8):3250-3259, The American Association of Immunologists, United States (1996).
Abbas, A.K., et al., Cellular and Molecular Immunobiology, 2nd ed., pp. 8, 47-50, W.B. Saunders Company, United States (1991).
Adams, G.P. and Weiner, L.M., "Monoclonal antibody therapy of cancer," Nature Biotechnology 23(9):1147-1157, Nature Publishing Group, United States (2005).
Affidavit of Christopher Butler, Apr. 23, 2014, 8 pages.
Alignment of Amino Acid Sequences for Extracellular Domain of Wild-Type (UniProt Q15116) Human PD-1, Wild-Type (MednaBio) PD-1 ECD, C62S Variant of Wild-Type Human PD-1 ECD, and A101L Variant of Wild-Type Human PD-1 ECD, 1 page, submitted with opposition on Apr. 30, 2014.
Amended Complaint, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, C.A. No. 14-cv-1131-GMS, United States District Court for the District of Delaware, Nov. 21, 2014, 11 pages.
Answer to Plaintiffs' Amended Complaint, *Bristol-Myers Squibb Co., E.R. Squibb & Sons L.L.C., Ono Pharmaceutical Co., Ltd., and Tasuku Honjo v. Merck & Co., Inc. and Merck Sharp & Dohme Corp.*, C.A. No. 14-cv-1131-GMS, United States District Court for the District of Delaware, Dec. 8, 2014, 17 pages.
Ansari, M.J., et al., "The programmed death-1 (PD-1) pathway regulates autoimmune diabetes in nonobese diabetic (NOD) mice," The Journal of Experimental Medicine 198(1):63-69, The Rockefeller University Press, United States (Jul. 2003).
Anti-Human CD279 (PD-1) Datasheet, 14-2799, J105, eBioscience, Sep. 6, 2013, 1 page.
Anti-Human CD279 (PD-1) Datasheet, 14-9989, J116, eBioscience, Sep. 6, 2013, 1 page.
Anti-Human CD279 (PD-1) Purchase Receipts, eBioscience, Oct. 8, 2013, 4 pages.
Appendix to Declaration of Vassiliki A. Boussiotis, Apr. 28, 2014, Data and Records for Example Experiments 21 and 22, 18 pages.
Berg, J.M., et al., "The Immune System," in Biochemistry 5th ed., pp. 921-950, W.H. Freeman and Company, United States (2002).
Berger, R., et al., "Phase I safety and pharmacokinetic study of CT-011, a humanized antibody interacting with PD-1, in patients with advanced hematologic malignancies," Clinical Cancer Research 14(10):3044-3051, American Association for Cancer Research, United States (2008).
Biacore, "Application Note 1: Characterization of monoclonal antibody epitope specificity using Biacore's SPR technology," Biacore AB, 8 pages (2002).
Biacore, Sensor Surface Handbook, BR-1005-71, edition AB, pp. 1-98, GE Healthcare (2005).
Biacore, "The SPR signal,""Interpreting experimental data," and "BIA application areas," in BIAtechnology Handbook, version AB, chapters 4-6, 34 pages, Biacore AB (1998).
Blank, C., et al., "Interaction of PD-L1 on tumor cells with PD-1 on tumor-specific T cells as a mechanism of immune evasion: implications for tumor immunotherapy," Cancer Immunology Immunotherapy 54(4):307-314, Springer-Verlag, Germany (2005).
Blank, C., et al.,"PD-L1/B7H-1 inhibits the effector phase of tumor rejection by T cell receptor (TCR) transgenic CD8+ T cells," Cancer Research 64(3):1140-1145, American Association for Cancer Research, United States (2004).
Brahmer., J.R., et al., "Phase I study of single-agent anti-programmed death-1 (MDX-1106) in refractory solid tumors: Safety, clinical activity, pharmacodynamics, and immunologic correlates." Journal of Clinical Oncology 28(19):3167-3175, American Society of Clinical Oncology, United States (2005).
Campbell, A.M., "Characterisation of monoclonal antibodies," in Laboratory Techniques in Biochemistry and Molecular Biology, Monoclonal Antibody Technology: The Production and Characterization of Rodent and Human Hybridomas, vol. 13, pp. 186-215, Elsevier, the Netherlands (1984).

(56) References Cited

OTHER PUBLICATIONS

Carreno, B.M. And Collins, M., "The B7 family of ligands and its receptors: new pathways for costimulation and inhibition of immune responses," Annual Review of Immunology 20:29-53, Annual Reviews, United States (Oct. 2002).
Carreno, B.M., "BTLA: a new inhibitory receptor with a B7-like ligand," TRENDS in Immunology 24(10):524-527, Elsevier, England (Oct. 2003).
Carter, L.L. and Carreno, B.M., et al., "Cytotoxic T-lymphocyte antigen-4 and programmed death-1 function as negative regulators of lymphocyte activation," Immunologic Research 28(1):49-59, Humana Press, United States (Aug. 2003).
Carter, L.L., et al., "PD-1:PD-L inhibitory pathway affects both CD4(+) and CD8(+) T cells and is overcome by IL-2," European Journal of Immunology 32(3):634-643, Wiley-VCH Verlag GmbH, German (Feb. 2002).
CD279/PD-1, D132-3/J110 Datasheet, MBL Medical & Biological Laboratories Co., Ltd., Sep. 6, 2013, 2 pages.
Chen, L., "Co-inhibitory molecules of the B7-CD28 family in the control of T-cell immunity," Nature Reviews Immunology 4(5):336-347, Nature Publishing Group, England (2004).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).
Clark, M.R., "Antibody engineering IgG effector mechanisms," Chemical Immunology 65:88-110 (1997), reprint from http://www.path.cam.ac.ukfmrc7 /publications/reprints/PP 1997CI65 88.pdf.
Cloeckaert, A., et al., "O-Polysaccharide epitopic heterogeneity at the surface of *Brucella* spp. studied by enzyme-linked immunosorbent assay and flow cytometry," Clinical and Diagnostic Laboratory Immunology 5(6):862-870, American Society for Microbiology, United States (1998).
Communication pursuant to Article 94(3) EPC mailed Apr. 23, 2014 for EP Application No. 06786260.7.
Ozaki, S., et al., "Immunotherapy of multiple myeloma with a monoclonal antibody directed against a plasma cell-specific antigen, HM1.24," Blood 90(8):3179-3186, American Society of Hematology, United States (1997).
Schmidt, M., et al., "Synergistic interaction between an anti-p185$^{HER-2}$ pseudomonas exotoxin fusion protein [scFv(FRP5)-ETA] and ionizing radiation for inhibiting growth of ovarian cancer cells that overexpress HER-2," Gynecologic Oncology 80(2):145-155, Academic Press, United States (2001).
Communication pursuant to Rule 114(2) EPC, mailed Jul. 17, 2014, Third Party Observations (Article 115 EPC) for Application No. EP20110178187.
Communication pursuant to Rule 114(2) EPC, mailed Jul. 17, 2014, Third Party Observations (Article 115 EPC) for Application No. EP20110178188.
Communication pursuant to Rule 114(2) EPC, mailed Jul. 17, 2014, Third Party Observations (Article 115 EPC) for Application No. EP20110178191.
Complaint, *Bristol-Myers Squibb Co. and Ono Pharmaceutical Co., Ltd.* v. *Merck & Co., Inc.*, 1:14-cv-01131-GMS, filed Sep. 4, 2014, 9 pages.
Co-pending U.S. Appl. No. 14/547,026, inventors Korman, A.J., et al., filed Nov. 18, 2014 (Not Published).
Wu, K-P., et al.. "Structural Basis of a Flavivirus Recognized by Its Neutralizing Antibody: Solution Structure of the Domain III of the Japanese Encephalitis Virus Envelope Protein," The Journal of Biological Chemistry 278(46):46007-46013, American Society for Biochemistry and Molecular Biology, Inc., United States (Nov. 2003).
Cox, J.P., et al., "A directory of human germ-line VX segments reveals a strong bias in their usage," European Journal of Immunoloy 24(4):827-836, Verlag Chemie GmbH, Germany (1994).
Cragg, M.S., et al., "Complement-mediated lysis by anti-CD20 mAb correlates with segregation into lipid rafts," Blood 101(3):1045-1052, American Society of Hematology, United States (Feb. 2003).
Cruse, J.M. and Lewis, R.E., "Antigens and Immunogens," in Atlas of Immunology, 2nd ed., pp. 105-126, CRC Press, United States (2004).
Curriculum Vitae of Dr. Robert J. Bloch, Apr. 11, 2012, 34 pages.
Curriculum Vitae of Vassiliki A. Boussiotis, Nov. 8, 2013, 24 pages.
Davies, D.R. and Cohen, G.H., "Interactions of protein antigens with antibodies." Proceedings of the National Academy of Sciences USA 93(1):7-12, National Academy of Sciences, United States (1996).
Declaration of Dr. Andrea Van Elsas, including Annex A and B, Apr. 29, 2014, 17 pages.
Declaration of Dr. Haidong Dong, Mar. 31, 2014, 15 pages.
Declaration of Dr. Jennifer Mataraza, Apr. 28, 2014, 11 pages.
Declaration of Dr. Robert J. Bloch, Apr. 29, 2014, 82 pages.
Declaration of Vassiliki A. Boussiotis, Apr. 28, 2014, 15 pages.
Del Rio, M-L., et al., "Antibody-mediated signaling through PD-1 costimulates T cells and enhances CD28-dependent proliferation," European Journal of Immunology 35(12):3545-3560, Wiley-VCH Verlag GmbH & Co. KGaA, Germany (2005).
Dong, H. and Chen, L., "B7-H1 pathway and its role in the evasion of tumor immunity," Journal of Molecular Medicine 81(5):281-287, Springer, Germany (May 2003).
Dougan, D.A., et al., "Effects of substitutions in the binding surface of an antibody on affinity," Protein Engineering 11(1):65-74, Oxford University Press, England (1998).
Email from MednaBio to Robert Bloch re: E1951MG1-Sequence Information, Apr. 25, 2014, 1 page.
Exhibit 1 "Human anti-PD-1 antibodies: binding to PD-1, cross-competition with 5C4 and affinity to PD-1," 6 pages, in Notice of Opposition mailed Apr. 29, 2014, in EP Patent No. EP 2161336, 4-Antibody AG filed May 2, 2006.
ExPASy Bioinformatics Resource Portal calculation based on ECD of UniProt Sequence Q15116, accessed at http://web.expasy.org/cgi-bin/compute_pi/pi_tool, accessed on Apr. 28, 2014, 1 page.
Extended European Search Report for EP Application No. 06746353.9, European Patent Office, Germany, mailed on Mar. 6, 2009.
Extended European Search Report for EP Application No. 09013687.0, European Patent Office, Germany, mailed on Jan. 29, 2010.
Communication pursuant to Article 94(3) EPC for EP Application No. 10161767.8, European Patent Office, Netherlands, mailed on Oct. 5, 2010.
Extended European Search Report for EP Application No. 10172772.5, European Patent Office, Netherlands, mailed on Sep. 9, 2010.
Extended European Search Report for EP Application No. 11178187.8, European Patent Office, Germany, mailed on Jun. 1, 2012.
Extended European Search Report for EP Application No. 11178188.6, European Patent Office, Germany, mailed on Jun. 27, 2013.
Extended European Search Report for EP Application No. 11178191.0, European Patent Office, Germany, mailed on Sep. 5, 2012.
Finger, L.R., et al., "The human PD-I gene: complete cDNA, genomic organization, and developmentally regulated expression in B cell progenitors," Gene 197(1-2):177-187, Elsevier, United States (1997).
Answer to Complaint, *Bristol-Myers Squibb Co., E.R. Squibb & Sons L.L.C., Ono Pharmaceutical Co., Ltd., and Tasuku Honjo* v. *Merck & Co., Inc. and Merck Sharp & Dohme Corp.*, C.A. No, 14-cv- 1131-GMS, United States District Court for the District of Delaware, Oct. 31, 2014, 15 pages.
Fivash, M., et al., "BIAcore for macromolecular interaction," Current Opinion in Biotechnology 9(1):97-101, Current Biology, England (1998).
Franklin, M.C., et al., "Insights into ErbB signaling from the structure of the ErbB2-pertuzumab complex," Cancer Cell 5(4):317-328, Cell Press, United States (2004).
Ge, X., et al., "CD134-Allodepletion Allows Selective Elimination of Alloreactive Human T Cells without Loss of Virus-Specific and Leukemia-Specific Effectors," Biology of Blood and Marrow Transplantation 14(5):518-530, American Society for Blood and Marrow Transplantation, United States (2008).
Greenspan, N.S., "Epitopes, paratopes and other topes: do immunologists know what they are talking about?" Bulletin de l'Institut Pasteur 90(4):267-279, Elsevier, France (1992).
Hansen, J.A., et al., "Monoclonal Antibodies Identifying a Novel T-Cell Antigen and Ia Antigens of Human Lymphocytes," Immunogenetics 10:247-260, Springer-Verlag (1980).

(56) References Cited

OTHER PUBLICATIONS

Harlow, E. and Lane, D., "Using Antibodies: A Laboratory Manual," Cold Spring Harbor Laboratory Press, Cold Spring Harbor, United States various pages (1999).

He, Y-F., et al.,"Blocking programmed death-1 ligand-PD-1 interactions by local gene therapy results in enhancement of antitumor effect of secondary lymphoid tissue chemokine," The Journal of Immunology 173(8):4919-4928, The American Association of Immunologists, United States (2004).

Hirano, F., et al., "Blockade of B7-H1 and PD-1 by monoclonal antibodies potentiates cancer therapeutic immunity," Cancer Research 65(3):1089-1096, American Association for Cancer Research, United States (2005).

Honjo, T., et al., Deposit receipt for Accession No. FERM BP-8392 mentioned in EP-A1537878, Jun. 5, 2003, 1 page.

Hutloff, A., et al.,"ICOS is an inducible T-cell co-stimulator structurally and functionally related to CD28," Nature 397(6716):263-266, Nature Publishing Group, England (1999).

International Preliminary Report on Patentability for International Application No. PCT/JP2006/309606, The International Bureau of WIPO, Switzerland, issued on Nov. 13, 2007.

International Search Report for International Application No. PCT/JP02/08420, Japanese Patent Office, Japan, mailed Nov. 5, 2002.

International Search Report for International Application No. PCT/JP2006/309606, Japanese Patent Office, Japan, mailed on Aug. 15, 2006.

Ishida, Y., et al., "Induced expression of PD-1, a novel member of the immunoglobulin gene superfamily, upon programmed cell death," The EMBO Journal 11(11):3887-3895, Oxford University Press, England (1992).

Ishima, R. and Torchia, D.A., "Protein Dynamics from NMR," Nature Structural Biology 7(9):740-743, Nature Publishing Company, United States (2000).

Witness Statement of Masako Ikeda, including exhibits A-E, Apr. 15, 2014, 20 pages.

Iwai, Y., et al., "PD-1 blockade inhibits hematogenous spread of poorly immunogenic tumor cells by enhanced recruitment of effector T cells," International Immunology 17(2):133-144, Oxford University Press, England (2005).

Iwai, Y., et al., "PD-1 inhibits antiviral immunity at the effector phase in the liver," The Journal of Experimental Medicine 198(1):39-50, The Rockefeller University Press, United States (Jul. 2003).

J105/D133-3 Datasheet, MBL Medical & Biological Laboratories Co., Ltd., Mar. 20, 2013, 2 pages.

J105/D133-3 Purchase Order, MBL Medical & Biological Laboratories Co., Ltd., Apr. 11, 2014, 1 page.

J105/D133-3 Purchase Receipts, Invoice MINV52635, MBL International Corporation, Oct. 2, 2013, 2 pages.

Janeway, C.A., et al. "The Humoral Immune Response," in Immunobiology: The immune system in health and disease, Sixth Edition, Chapter 9, pp. 367-408, Garland Science, New York, United States (2005).

Jason-Moller, L., et al., "Overview of Biacore Systems and Their Applications," Current Protocols in Protein Science S45:19.13.1-19.13.14, John Wiley & Sons, Inc., United States (2006).

Johne, B., "Protocol: Epitope Mapping by Surface Plasmon Resonance in the BIAcore," Molecular Biotechnology 9(1):65-71, Humana Press, United States (1998).

Kanai, T., et al., "Blockade of B7-H1 Suppresses the Development of Chronic Intestinal Inflammation," The Journal of Immunology 171(8):4156-4163, American Association of Immunologists, Inc., United States (Oct. 2003).

Kasagi, S., et al., "Anti-programmed cell death 1 antibody reduces CD4+PD-1+ T cells and relieves the lupus-like nephritis of NZB/W F1 mice," The Journal of Immunology 184(5):2337-2347, The American Association of Immunologists, United States (2010).

Kaveri, S., "Epitope and idiotope mapping using monoclonal antibodies," Methods in Molecular Biology 51:171-181, Humana Press, United States (1995).

Koga, N., et al., "Blockade of the interaction between PD-1 and PD-L1 accelerates graft arterial disease in cardiac allografts," Arteriosclerosis, Thrombosis, and Vascular Biology 24(11):2057-2062. American Heart Association, Inc., United States (2004).

Konishi, J., et al., "B7-H1 expression on non-small cell lung cancer cells and its relationship with tumor-infiltrating lymphocytes and their PD-1 expression," Clinical Cancer Research 10(15):5094-5100, American Association for Cancer Research, United States (2004).

Ladner, R.C. "Mapping the Epitopes of Antibodies," Biotechnology and Genetic Engineering Reviews 24(1):1-30, Taylor & Francis, England (2007).

Laricchia-Robbio, L., et al., "Mapping of Monoclonal Antibody- and Receptor-Binding Domains on Human Granulocyte-Macrophage Colony-Stimulating Factor (rhGM-CSF) Using a Surface Plasmon Resonance-Based Biosensor," Hybridoma 15(5):343-350, Mary Ann Lieberl, Inc., United States (1996).

Leach, D.R., et al., "Enhancement of antitumor immunity by CTLA-4 blockade," Science 271(5256):1734-1736, American Association for the Advancement of Science, United States (1996).

Lewis, D.E., et al., "Tumor Necrosis Factor-α and CD80 Modulate CD28 Expression through a Similar Mechanism of T-cell Receptor-Independent Inhibition of Transcription," The Journal of Biological Chemistry 279(28):29130-29138, The American Society for Biochemistry and Molecular Biology, Inc., United States (2004).

Li, L., et al.,"A pathway regulated by cell cycle inhibitor p27Kip1 and checkpoint inhibitor Smad3 is involved in the induction of T cell tolerance," Nature Immunology 7(11):1157-1165, Nature Publishing, United States (2006).

Li, L., et al., "CD4+CD25+ regulatory T-cell lines from human cord blood have functional and molecular properties and T-cell anergy," Blood 106(9):3068-3073, American Society of Hematology, United States (2005).

Li, L., et al., "IL-1beta-Mediated Signals Preferentially Drive Conversion of Regulatory T Cells but Not Conventional T Cells into IL-17-Producing Cells," The Journal of Immunology 185(7):4148-4153, American Association of Immunologists, Inc., United States (2010).

Li, L., et al., "Rap1-GTP is a Negative Regulator of Th Cell Function and Promotes the Generation of CD4+CD103+ Regulatory T Cells In Vivo," The Journal of Immunology 175(5):3133-3139, American Association of Immunologists. Inc., United States (2005).

Li, L., at al., "The cyclin dependent kinase inhibitor (R)-roscovitine prevents alloreactive T cell clonal expansion and protects against acute GvHD," Cell Cycle 8(11):1794-1802, Landes Bioscience, United States (2009).

Lonberg, N., et al., "Antigen-specific human antibodies from mice comprising four distinct genetic modifications," Nature 368(6474):856-859, Nature Publishing Group, United States (1994).

Lute, K.D., et al., "Human CTLA4 knock-in mice unravel the quantitative link between tumor immunity and autoimmunity induced by anti-CTLA-4 antibodies," Blood 106(9):3127-3133, American Society of Hematology, United States (2005).

May, K.F., Jr., et al., "Anti-human CTLA-4 monoclonal antibody promotes T-cell expansion and immunity in a hu-PBL-SCID model: a new method for preclinical screening of costimulatory monoclonal antibodies," Blood 105(3):1114-1120, American Society of Hematology, United States (2005).

Nagler, A., et al., "Phase I clinical trial of CT-011, a humanized monoclonal antibody directed against a B7 family-associated protein, in patients with advanced hematological malignancies," 34th Annual Meeting: ISEH—Abstracts/Experimental Hematology 33(7):97, Abstract No. 227, Elsevier, United States (2005).

Nellore, A., et al., "The cyclin dependent kinase inhibitor (R)-roscovitine mediates selective suppression of alloreactive human T cells but preserves pathogen-specific and leukemia-specific effectors," Clinical Immunology 152(1-2):48-57 (May-Jun. 2014; Epub Mar. 12, 2014).

Nielsen, C., et al., "A putative regulatory polymorphism in PD-1 is associated with nephropathy in a population-based cohort of systemic lupus erythematosus patients," Lupus 13(7):510-516, SAGE, England (2004).

(56) References Cited

OTHER PUBLICATIONS

Nishimura, H., et al., "Autoimmune dilated cardiomyopathy in PD-1 receptor-deficient mice," Science 291(5502):319-322, American Association for the Advancement of Science, United States (2001).

Nishimura, H., et al.,"Development of lupus-like autoimmune diseases by disruption of the PD-1 gene encoding an ITIM motif-carrying immunoreceptor," Immunity 11(2):141-151, Cell Press, United States (1999).

Nomi, T., et al., "Clinical significance and therapeutic potential of the programmed death-1 ligand/programmed death-1 pathway in human pancreatic cancer," Clinical Cancer Research 13(7):2151-2157, The Association, United States (2007).

Non-Final Office Action mailed Feb. 21, 2014, in U.S. Appl. No. 13/210,137, Korman, A.J., et al., filed Aug. 15, 2011.

Non-Final Office Action mailed Oct. 25, 2010, in U.S. Appl. No. 11/913,217, Korman, A. J., et al., filed Jan. 29, 2009.

Yi, J., et al., "Mapping the Epitope of an Inhibitory Monoclonal Antibody to the C-terminal DNA-binding Domain of HIV-1 Integrase," The Journal of Biological Chemistry 277(14):12164-12174, American Society for Biochemistry and Molecular Biology, Inc., United States (Apr. 2002).

Zhang, X., et al., "Structural and functional analysis of the costimulatory receptor programmed death-1," Immunity 20(3):337-347, Cell Press, United States (2004).

Notice of Opposition mailed Apr. 25, 2014, in EP Patent No. EP 2161336, Novartis A.G., filed May 2, 2006.

Notice of Opposition mailed Apr. 29, 2014, in EP Patent No. EP 2161336, 4-Antibody AG filed May 2, 2006.

Notice of Opposition mailed Apr. 30, 2014, in EP Patent No. EP 2161336, Janssen Biotech, Inc., filed May 2, 2006.

Notice of Opposition mailed Apr. 30, 2014, in EP Patent No. EP 216 336, Merck & Co., Inc., filed May 2, 2006.

Okazaki, T., et al., "New regulatory co-receptors: inducible co-stimulator and PD-1," Current Opinion in Immunology 14(6):779-782, Elsevier, England (Dec. 2002).

Okazaki, T., et al., "PD-1 immunoreceptor inhibits B cell receptor-mediated signaling by recruiting src homology 2-domain-containing tyrosine phosphatase 2 to phosphotyrosine," Proceedings of the National Academy of Sciences 98(24):13866-13871, National Academy of Sciences, United States (2001).

Panka, D.J., et al., "Variable region framework differences result in decreased or increased affinity of variant anti-digoxin antibodies," Proceedings of the National Academy of Sciences 85(9):3080-3084, National Academy of Sciences, United States (1988).

Park, J.W. and Smolen, J., "Monoclonal antibody therapy," Advances in Protein Chemistry 56:369-421, Academic Press, United States (2001).

Patent Assignment Abstract of Title for U.S. Patent No. 8,008,449, USPTO Assignments on the Web, accessed on Apr. 30, 2014, 2 pages.

Patentee's response to Examination Report for EP Application No. 09013687.0, mailed Apr. 4, 2012.

Patsoukis, N., et al., "Selective Effects of PD-1 on Akt and Ras Pathways Regulate Molecular Components of the Cell Cycle and Inhibit T Cell Proliferation," Science Signaling 5(230): ra46, pp. 1-14, American Association for the Advancement of Science, United States (2012).

Patsoukis, N., et al., "PD-1 Increases PTEN Phosphatase Activity While Decreasing PTEN Protein Stability by Inhibiting Casein Kinase 2," Molecular and Cellular Biology 33(16):3091-3098, American Society for Microbiology, United States (2013).

Patsoukis, N., et al., "PD-1 inhibits T cell proliferation by upregulating p27 and p15 and suppressing Cdc25A," Cell Cycle 11(23):1-5, Landes Bioscience, United States (2012).

Polyak, M.J. And Deans, J.P., "Alanine-170 and proline-172 are critical determinants for extracellular CD20 epitopes; heterogeneity in the fine specificity of CD20 monoclonal antibodies is defined by additional requirements imposed by both amino acid sequence and quaternary structure," Blood 99(9):3256-3262, American Society of Hematology, United States (May 2002).

Product Specifications for AffiniPure Goat Anti-Human IgG, Fcγ Fragment Specific (minimal cross-reaction to Bovine, Horse, and Mouse Serum Proteins), Code No. 109-005-098, Lot No. 111632, Jackson ImmunoResearch Laboratories, Inc., Sep. 12, 2013, 1 page.

Product Specifications for AffiniPure Goat Anti-Mouse IgG, Fcγ Fragment Specific (minimal cross-reaction to Human, Bovine, and Horse Serum), Code No. 115-005-071, Lot No. 111143, Jackson ImmunoResearch Laboratories, Inc., Sep. 12, 2013, 1 page.

Prokunina, L. and Alarcon-Riquelme, M., "The genetic basis of systemic lupus erythematosus—knowledge of today and thoughts for tomorrow," Human Molecular Genetics 13(1):R143-R148, Oxford University Press, England (2004).

Response to Non-Final Office Action mailed Jan. 25, 2011, in U.S. Appl. No. 11/913,217, Korman, A.J., et al., filed Jan. 29, 2009.

Response to Non-Final Office Action mailed Mar. 4, 2014, in U.S. Appl. No. 13/210,137, Korman, A. J., et al., filed Aug. 15, 2011.

Response to request further processing of EP Application No. 11178191.0, mailed on mailed Mar. 20, 2014, 11 pages.

Rudikoff, S., et al., "Single amino acid substitution altering antigen-binding specificity," Proceedings of the National Academy of Sciences 79(6):1979-1983, The National Academy of Sciences, United States (1982).

Salama, A.D., et al., "Critical role of the programmed death-1 (PD-1) pathway in regulation of experimental autoimmune encephalomyelitis," The Journal of Experimental Medicine 198(1):71-78, The Rockefeller University Press, United States (Jul. 2003).

Andre, E., et al., "Precise Characterization of the Epitope Recognized by a Monoclonal Antibody Against *Escherichia coli* RNA Polymerase," Hybridoma 24(1):1-5, Mary Ann Liebert, Inc., United States (2005).

Sequence alignments between PD-1 and each of CTLA-4, CD28 and ICOS, accessed at http://www.ebi.ac.uk/Tools/services/web/toolresult.ebi?jobld=clustalo-120- 140410-15, accessed on Apr. 10, 2014.

Shinohara, T., et al., "Structure and chromosomal localization of the human PD-1 gene (PDCD1)," Genomics 23(3):704-706, Academic Press, United States (1994).

Singer, M. and Berg, P., "Genes and Genomes," in University Science Books, 1:63-64, Sausalito, United States (1998).

Teeling, J.L., et al., "Characterization of new human CD20 monoclonal antibodies with potent cytolytic activity against non-Hodgkin lymphomas," Blood 104(6):1793-1800, American Society of Hematology, United States (2004).

Thomas, M.L., "Of ITAMs and ITIMs: turning on and off the B cell antigen receptor," The Journal of Experimental Medicine 181(6):1953-1956, The Rockefeller University Press, United States (1995).

Tomlinson, I.M., et al., "The repertoire of human germline VH sequences reveals about fifty groups of VH segments with different hypervariable loops," Journal of Molecular Biology 227(3):776-798, Elsevier, Netherlands (1992).

Tsai, C-J., et al., "Protein allostery, signal transmission and dynamics: a classification scheme of allosteric mechanisms," Molecular BioSystems 5(3):207-216, Royal Society of Chemistry, England (2009).

UniProtKB/Swiss-Prot Database entry, PDCD1_HUMAN, accessed at http://www.uniprot.org/uniprot/Q15116.txt, accessed on Apr. 29, 2014, 5 pages.

UniProtKB/Swiss-Prot, Q15116 (PDCD1_HUMAN), version 126, 8 pages, last modified on Apr. 16, 2014.

Van Regenmortel, M.H.V., "The Recognition of Proteins and Peptides by Antibodies," Journal of Immunoassay 21(2-3):85-108, Taylor & Francis, England (2000).

Van Regenmortel, M.H.V., "Structural and functional approaches to the study of protein antigenicity," Immunology Today 10(8):266-272, Elsevier Science Publishers, England (1989).

Vivier, E. and Daeron, M., "Immunoreceptor tyrosine-based inhibition motifs," Immunology Today 18(6):286-291, Elsevier, England (1997).

Wilson, I.A. and Stanfield, R.L., "Antibody-antigen interactions," Current Opinion in Structural Biology 3:113-118, Current Biology, United States (1993).

(56) References Cited

OTHER PUBLICATIONS

Witness Statement of Hiroyuki Yamada, including exhibits 1-7, Apr. 16, 2014, 46 pages.
Soh, E.Y., et al.,"Neutralizing vascular endothelial growth factor activity inhibits thyroid cancer growth in vivo," Surgery 128(6):1059-1066, Mosby, United States (2000).
Allison, J.P. and Krummel, M.F., "The Yin and Yang of T Cell Costimulation," Science 270(5238):932-933, American Association for the Advancement of Science, United States (1995).
Ansell, S.M., et al., "PD-1 Blockade with Nivolumab in Relapsed or Refractory Hodgkin's Lymphoma," The New England Journal of Medicine 372(4):311-319, Massachusetts Medical Society, United States (Jan. 22, 2015).
Armand, P., et al., "289 Nivolumab in Patients with Relapsed or Refractory Hodgkin Lymphoma—Preliminary Safety, Efficacy and Biomarker Results of a Phase I Study," 56th ASH Annual Meeting and Exposition, Abstracts & Program, San Francisco, CA, Dec. 6-9, 2014.
"List of Clinical Trials with Nivolumab from the website ClinicalTrials.gov of U.S. National Institutes of Health" submitted with Response to Oppositions against EP Pat. No. 2161336, mailed on Feb. 16, 2015, 11 pages.
Communication pursuant to Article 94(3) EPC mailed on Dec. 22, 2014, in European Application No. 11 178 187.8-1410, European Patent Office, Germany.
Communication pursuant to Article 94(3) EPC mailed on Dec. 22, 2014, in European Application No. 11 178 191.0-1410, European Patent Office, Germany.
Co-pending U.S. Appl. No. 14/638,985, filed Mar. 4, 2015, Honjo, T., et al., (Not Publsihed).
Curriculum Vitae of Brian T. Fife, Ph.D., submitted with Response to Oppositions against EP Pat. No. 2161336, mailed on Feb. 16, 2015, 7 pages.
Unpublished 2003 Data Compilation ONK014_004_0000003, 446 pages.
Unpublished 2004-2005 Data Compilation ONK014_005_0000003, 538 pages.
Unpublished 2003 Data Compilation ONK015_001_0000003, 50 pages.
Unpublished 2003-2004 Data Compilation ONK23_005_0000003, 476 pages.
Unpublished 2003 Data Compilation, UBIC_Control_00010079343, 38 pages.
Declaration of Professor Brian T. Fife, Feb. 12, 2015, submitted with Response to Oppositions against EP Pat. No. 2161336, mailed on Feb. 16, 2015, 4 pages.
Lesokhin, A.M., et al., "291 Preliminary Results of a Phase I Study of Nivolumab (BMS-936558) in Patients with Relapsed of Refractory Lymphoid Malignancies," 56th ASH Annual Meeting and Exposition, Abstracts & Program, San Francisco, CA, United States, Dec. 6-9, 2014.
Office Action mailed Apr. 13, 2015, in U.S. Appl. No. 14/638,985, inventors Honjo, T., et al., filed Mar. 4, 2015.
Ono Pharmaceutical Co., Ltd Research Center Search Research Institute, Ryoji Yagi (Test Director), "Study of the Antitumor Effects of Anti-mouse PD-1 (J43) in Mouse J558 Cell (myeloma) Subcutaneous Implantation Methods," Final Report, Test No. E03CT01 1, (planned test period: 2003-2004), 34 pages.
Press Release from Bristol-Myers Squibb, "Bristol-Myers Squibb Receives Accelerated Approval of Opdivo (nivolumab) from the U.S. Food and Drug Administration," Dec. 22, 2014, 6 pages.
Press Release from ESMO, "ESMO 2014 Press Release: Nivolumab Shows Signs of Superior Response Rate Compared to Standard Chemotherapy in Advanced Melanoma," Sep. 29, 2014, 2 pages.
Press Release from Ono Pharmaceuticals Co., Ltd., "Human Anti-human PD-1 Monoclonal Antibody "Opdivo(R) Intravenous Infusion 20 mg/100 mg" Receives Manufacturing and Marketing Approval in Japan for the Treatment of Unresectable Melanoma," Jul. 4, 2014, 2 pages.
Press-Release from Bristol-Myers Squibb, "CheckMate-017, A Phase 3 Study of Opdivo (Nivolumab) Compared to Docetaxel in Patients with Second-Line Squamous Cell Non-small Cell Lung Cancer, Stopped Early," Jan. 11, 2015, 5 pages.
Press-Release from Bristol-Myers Squibb, "Phase 3 First-Line Melanoma Study of Nivolumab, an Investigational PD-1 Checkpoint Inhibitor, Demonstrates Superior Overall Survival Compared to Dacarbazine; Study Stopped Early," Jun. 24, 2014, 3 pages.
Product Insert for Opdivo(R) (nivolumab), Bristol-Myers Squibb Company, United States, issued Mar. 2015.
Response to Oppositions, mailed Feb. 16, 2015, in European Patent No. EP 2161336, Ono Pharmaceutical Co., Ltd. and Medarex, Inc, 27 pages.
Second Declaration of Andrea Van Elsas, Ph.D., including exhibits 1-3, Jan. 22, 2015, submitted with Statement of Grounds of Appeal for EP Pat. No. 1537878, mailed on Feb. 3, 2015, 67 pages.
Sho, M., et al., "Effect of Blocking T Cell Negative Pathway on Cancer Metastasis," Article for the Annual Meeting of the Japanese Cancer Association 64:59 (W-102) (2005).
Sho, M., et al., "Possibility of Clinical Applications for Novel Cancer Immunotherapy via Inhibition of T-cell Negative Pathway," Magazine of the Japan Society of Clinical Oncology 40(2):590 (PS22-5) (2005).
Statement of Grounds of Appeal mailed Feb. 3, 2015 for European Patent No. EP 1537 878, European Patent Office, Munich, Germany, 107 pages.
Summary of Clinical Trial List, Search of: Nivolumab, ClinicalTrials.gov, accessed at https://www.clinicaltrials.gov/ct2/results?term=nivolumab&pg=1, accessed on Feb. 9, 2015, 7 pages.
Tchekiviedyian, S., et al., Abstract 56, p. 15a and Davis, T.A., et al., Abstract 74, p. 19a, Proceedings of the American Society of Clinical Oncology, Thirty-Eighth Annual Meeting, Abstracts, Orlando, Florida, United States (May 18-21, 2002).
Topalian, S., et al., "Nivolumab (anti-PD-1; BMS-936558; ONO-4538) in patients with advanced solid tumors: Survival and long-term safety in a phase I trial, accessed at http://meetinglibrary.asco.org/content/113543-132," accessed on Feb. 2, 2015, 2 pages.
Wolchok, J.D., et al., "Nivolumab plus Ipilimurnab in Advanced Melanoma," The New England Journal of Medicine 369(2):122-133, Massachusetts Medical Society, United States (2013).
Product Insert for Keytruda(R) (pembrolizumab), Merck & Co., Inc., United States, issued 2014.

\* cited by examiner

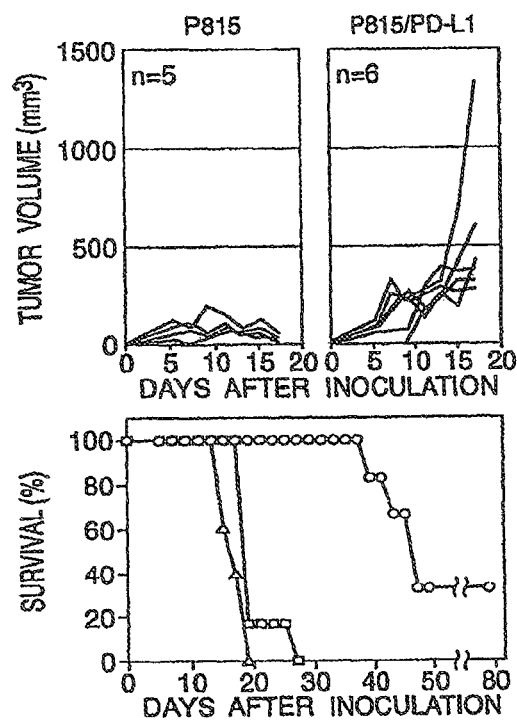
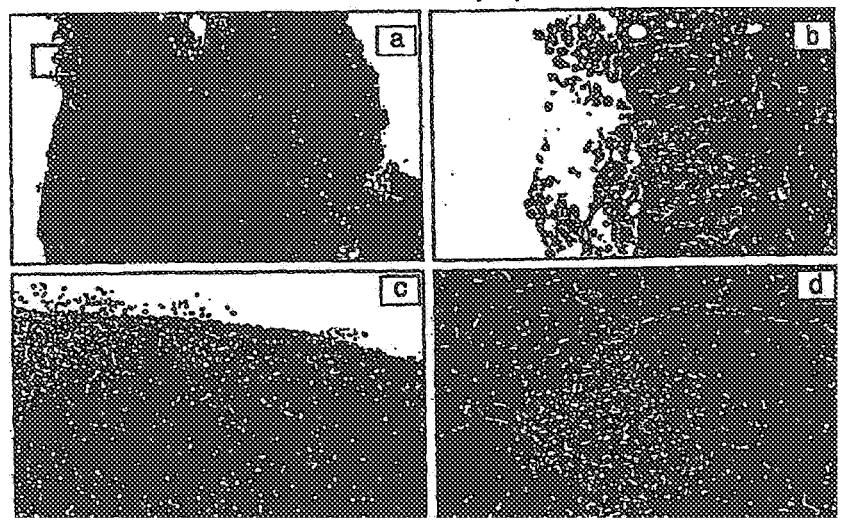

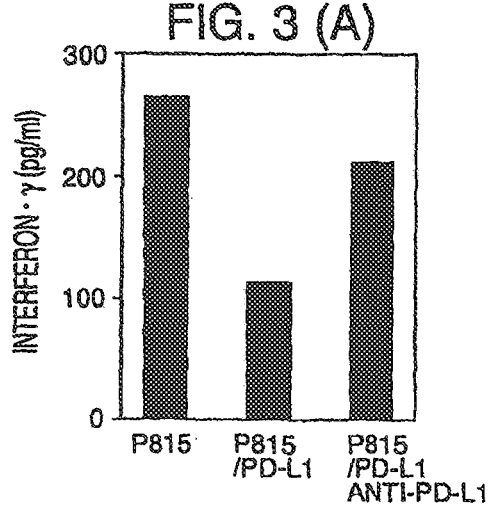
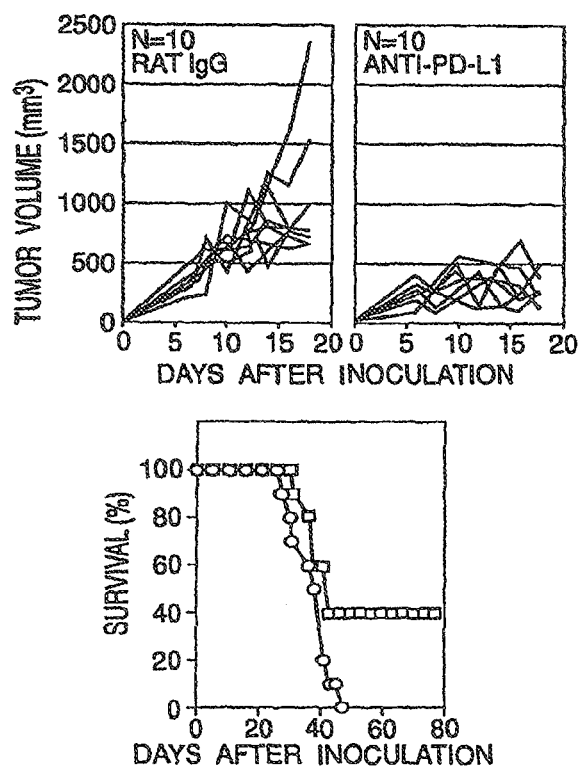

x 40

IMMUNOPOTENTIATIVE COMPOSITION

REFERENCE TO RELATED APPLICATIONS

This application is a divisional application of U.S. application Ser. No. 14/245,692, filed Apr. 4, 2014, which is a divisional application of U.S. application Ser. No. 12/959,307 (now U.S. Pat. No. 8,728,474), filed Dec. 2, 2010, which is a divisional application of U.S. application Ser. No. 12/538,698, filed Aug. 10, 2009 (now U.S. Pat. No. 8,168,179), which is a divisional application of U.S. application Ser. No. 10/519,925, filed Jan. 3, 2005 (now U.S. Pat. No. 7,595,048), which is a National Stage Entry of PCT/JP03/08420 filed Jul. 2, 2003, which claims priority to Japanese Patent Application Nos. 2002-194491 and 2003-029846 filed Jul. 3, 2002 and Feb. 6, 2003, respectively. The entire disclosures of the above-listed applications are hereby incorporated by reference in their entireties.

TECHNICAL FIELD

The present invention relates to immunopotentiation characterized by inhibiting immunosuppressive signals induced by PD-1, PD-L1 or PD-L2, compositions for cancer or infection treatment, and therapies that use them.

More specifically, the present invention relates to the compositions for cancer or infection treatment through an immunopotentiationn caused by inhibition of immunosuppressive signals induced by PD-1, PD-L1 or PD-L2, the therapies that use them, screening methods of immunopotentiative substances, or substances for cancer treatment or for infection treatment that are contained in the composition as an active ingredient, cell lines used for those screening methods, an evaluation that selects the substances for cancer treatment, and carcinoma cells transplanted mammals used for the evaluation.

BACKGROUND ART

Immunotherapies can reduce side reactions that can't be avoided easily in most chemotherapies, and is expected as a therapy with extremely high specificity. The immunotherapies can be executed in the purpose to recover patient's QOL by activating the immune reaction that human originally has by an extrinsic method and subrogating a part of the load by medication.

Immunopotentiation can be executed by methods of activating immune reaction of T lymphocytes. It is said that not only stimulation through antigen receptors (TCR) but also an additionally stimulative inducement through conjugated stimulative molecular groups (for example, CD28) could be necessary for the activation of T cells. However, it is reported that as the molecular groups with homologous structures to the conjugated stimulative molecular groups, CTLA-4 and PD-1 were discovered recently and give signals that suppress signals of antigen receptors (TCR). It is thought that a method of activating T cells could be an effective mean to suprress the function of those conjugated control molecules.

PD-1 was cloned as 55 kD of I type membrane protein that belong to an immunoglobulin family (The EMBO Journal (1992), vol. 11, issue 11, p. 3887-3895, JP5336973, JP7291996). Human PD-1 cDNA is composed of the base sequence shown in EMBL/GenBank Acc. No.NM_005018 and mouse PD-1 cDNA is composed of the base sequence shown in Acc. No.X67914, and those expression are observed when thymus cells differentiate from CD4-CD8- cell into CD4+ CD8+ cell (International Immunology (1996), vol. 18, issue 5, p. 773-780, Journal of Experimental Medicine (2000), vol. 191, issue 5, p. 891-898). It is reported that PD-1 expression in periphery is observed in myeloid cells including T cells or B lymphocytes activated by stimulation from antigen receptors, or activated macrophages (*International Immunology* (1996), vol. 18, issue 5, p. 765-772).

In an intracellular domain of PD-1, there are ITIM motifs (Immunoreceptor Tyrosine-based Inhibitory Motif) that could been thought to be a repression domain to immune reaction. Since PD-1-deficient mice develop lupus-like autoimmune disease such as glomerular nephritis and arthritis (for C57BL/6 gene background) (*International Immunology* (1998), vol. 10, issue 5502, p. 1563-1572, Immunity (1999), vol. 11, issue 2, p. 141-151) and a disease like dilated cardiomyopathy (for BALB/c gene background ) (*Science* (2001), vol. 291, issue 5502, p. 319-332), it has been suggested that PD-1 could be a control factor of development of autoimmune disease, especially the peripheral self-tolerance.

PD-L1 (human PD-L1 cDNA is composed of the base sequence shown by EMBL/GenBank Acc. No. AF233516 and mouse PD-L1 cDNA is composed of the base sequence shown by NM_021893) that is a ligand of PD-1 is expressed in so-called antigen-presenting cells such as activated monocytes and dendritic cells (*Journal of Experimental Medicine* (2000), vol. 19, issue 7, p 1027-1034). These cells present interaction molecules that induce a variety of immuno-inductive signals to T lymphocytes, and PD-L1 is one of these molecules that induce the inhibitory signal by PD-1. It has been revealed that PD-L1 ligand stimulation suppressed the activation (cellular proliferation and induction of various cytokine production) of PD-1 expressing T lymphocytes. PD-L1 expression has been confirmed in not only immunocompetent cells but also a certain kind of tumor cell lines (cell lines derived from monocytic leukemia, cell lines derived from mast cells, cell lines derived from hepatic carcinomas, cell lines derived from neuroblasts, and cell lines derived from breast carcinomas) (*Nature Immunology* (2001), vol. 2, issue 3, p. 261-267).

Though PD-L2 (human PD-L2 cDNA is composed of the base sequence shown by EMBL/GenBank Acc. No. NM_025239 and mouse PD-L2 cDNA is composed of the base sequence shown by NM_021896) had been identified as a second ligand of PD-1, it has been reported that the expression and function are almost same as PD-L1 (*Nature Immunology* (2001), vol. 2, issue 3, p. 261-267).

It has been thought that the inhibitory signals from the conjugated suppressive molecules represented by PD-1 could control abnormal immune reaction to autoantigen and immunological tolerance in lymphocyte generation or maturation by a mechanism that appropriately controls positive signals with antigen receptors (TCR) and conjugated stimulation molecules. It has been thought that a certain kind of tumour and virus could use those conjugated suppressive molecules to intercept the activation and proliferation of T cells and weaken the host immunity reaction to oneself by a direct or indirect mechanism (*Cell* (1992), vol. 71, issue 7, p. 1093-1102, *Science* (1993), vol. 259, issue 5093, p. 368-370). It has been thought that those conjugated suppressive molecules could have caused the impairment of T cells in a part of disease thought to originate in impairment of T cells.

DISCLOSURE OF THE INVENTION

A problem of the present invention is to provide compositions to activate immunity by inhibiting the inhibitory signals of PD-1, PD-L1 or PD-L2 and compositions for cancer or infection treatment through this mechanism.

The present inventors paid attention to PD-1, PD-L1, or PD-L2 as a new target in cancer or infection treatment and found that substances that inhibit the inhibitory signals of PD-1, PD-L1 or PD-L2 inhibit cancer proliferation through the mechanism of the recovery and activation of immune function. Further, they found that PD-1 signal, concretely, an interaction of PD-1 and PD-L1 or PD-1 and PD-L2 took part in the exclusion of infectious virus. According to those facts, they found the substances that could inhibit the inhibitory signals of PD-1, PD-L1 or PD-L2 having therapeutic potential for cancer or infection and completed the present invention.

That is, the present invention relates to 1. an immunopotentiative composition containing an immunosuppressive signal inhibitor of PD-1, PD-L1 or PD-L2,
2. a composition for cancer treatment containing the immunosuppressive signal inhibitor of PD-1, PD-L1 or PD-L2,
3. the composition for cancer treatment of the subsection 2, which is a composition that suppresses cancer metastasis,
4. a composition for infection treatment containing an immunosuppressive signal inhibitor of PD-1, PD-L1 or PD-L2,
5. the composition for cancer treatment of the subsection 2 or 3, which is characterized by acting through immunopotentiation,
6. the composition for infection treatment of the subsection 4, which are characterized by acting through immunopotentiation,
7. the composition of either of the subsection 1 to 6, which the immunosuppressive signal inhibitor is/are one or more selected from an interaction inhibitor of PD-1 and PD-L1 or PD-1 and PD-L2, an intracellular signaling inhibitor of PD-1, and an inhibitory substance of PD-1, PD-L1 or PD-L2 production,
8. the composition of the subsection 7, which is/are one or more of the interaction inhibitor(s) of PD-1 and PD-L1 selected from PD-1 antibody, PD-L1 antibody, soluble PD-1, and soluble PD-L1,
9. the composition of the subsection 8, which is PD-1 antibody selected from anti-human PD-1 antibody of which hybridomas identified by International Trust Number FERM BP-8392 product, anti-PD-1 antibody humanized from non-human antibody, and human type anti-human PD-1 antibody,
10. the composition of either of the subsection 1 to 6, which the immunosuppressive signal inhibitor is a lymphocyte of which PD-1 expression is inhibited by gene-recombination,
11. the composition of the subsection 7, which the interaction inhibitor of PD-1 and PD-L1 or PD-1 and PD-L2, an intracellular signaling inhibitor of PD-1, or the inhibitory substance of PD-1, PD-L1 or PD-L2 production is one or more of substance(s) selected from protein, polypeptide or peptide, polynucleotide or polynucleoside, antibody or the derivative, organic synthesis compound, inorganic compound, and natural product,
12. an immunopotentiative method containing a method of administering the immunosuppressive signal inhibitor of PD-1, PD-L1 or PD-L2,
13. a method for cancer treatment containing a method of administering the immunosuppressive signal inhibitor of PD-1, PD-L1 or PD-L2,
14. the method of cancer treatment of the subsection 13, which is a method of suppressing cancer metastasis,
15. a method for infection treatment containing a method of administering the immunosuppressive signal inhibitor of PD-1, PD-L1 or PD-L2,
16. the method for cancer treatment of the subsection 13 or 14, which is characterized by acting through immunopotentiation,
17. the method for infection treatment of the subsection 15, which is characterized by acting through immunopotentiation,
18. the method of either of the subsection 12 to 17, which the immunosuppressive signal inhibitor is/are one or more selected from the interaction inhibitor of PD-1 and PD-L1 or PD-1 and PD-L2, the intracellular signaling inhibitor of PD-1, and the inhibitory substance of PD-1, PD-L1 or PD-L2 production,
19. the method of the subsection 18, which the interaction inhibitor is/are one or more selected from PD-1 antibody, PD-L1 antibody, soluble PD-1, and soluble PD-L1,
20. the method of the subsection 19, which PD-1 antibody is an antibody selected from anti-human PD-1 antibody of which hybridomas identified by international trust number FERM BP-8392 product, anti-PD-1 antibody humanized from non-human antibody, and human type anti-human PD-1 antibody,
21. the method of either of the subsection 12 to 17, which the immunosuppressive signal inhibitor is a lymphocyte of which PD-1 expression is inhibited by gene-recombination.
22. the method of the subsection 18, which the interaction inhibitor of PD-1 and PD-L1 or PD-1 and PD-L2, the intracellular signaling inhibitor of PD-1, or the inhibitory substance of PD-1, PD-L1 or PD-L2 production are one or more of substance(s) selected from protein, polypeptide or peptide, polynucleotide or polynucleotide, antibody or the derivative, organic synthesis compound, inorganic compound, and natural product,
23. use of the immunosuppressive signal inhibitor of PD-1, PD-L1 or PD-L2 to manufacture the immunopotentiative composition,
24. use of the immunosuppressive signal inhibitor of PD-1, PD-L1 or PD-L2 to manufacture the composition for cancer treatment,
25. use of the substance of the subsection 24, which the composition for cancer treatment is the composition for suppression of cancer metastasis,
26. use of the immunosuppressive signal inhibitor of PD-1, PD-L1 or PD-L2 to manufacture the composition for infection treatment,
27. carcinoma cell lines for screening, which are transformed to express PD-L1 or PD-L2,
28. a screening method for the immunopotentiative substance characterized by touching the cells of the subsection 27 to lymphocytes and a subject substance, followed by evaluating the enhancement of the subject substance for immune reaction of lymphocytes to the cells of the subsection 27,
29. a screening method for a substance for cancer treatment characterized by touching the carcinoma cells of the subsection 27 to lymphocytes and a subject substance, followed by evaluating the enhancement of the subject substance for immune reaction of lymphocytes to carcinoma cells and inhibitory effect on the subject substance for carcinoma cells proliferation,
30. a screening method for a substance for infection treatment characterised by touching the infected cells of the subsection 27 to lymphocytes and a subject substance, followed by evaluating the enhancement of the subject substance for immune reaction of lymphocytes to the infected cells and inhibitory effect on the subject substances for pathogens proliferation, 31. a mammal created by transplant the carcinoma cell lines of the subsection 27, and 32. a screening method for a substance for cancer treatment characterized by administering the subject substance to the mammal of of the subsection 31, followed by evaluating the inhibitory ratio of the subject substance for the transplanted carcinoma cells proliferation.

PD-1, PD-L1, or PD-L2 of the present invention includes each one derived from mammal, for example, mouse, rat, hamster, guinea pig, dog, pig, ape, or primate including human. They are suitable to be human PD-L1, PD-1, and PD-L2, respectively.

The immunosuppressive signal of PD-1, PD-L1, or PD-L2 in the present invention is at least composed of the interaction of PD-1 and PD-L1 or PD-1 and PD-L2, and the intracellular signalings of PD-1. Production of PD-1, PD-L1 or PD-L2 itself is included in them.

The immunosuppressive signal of PD-1, PD-L1, or PD-L2 in the present invention is inhibited by direct or indirect inhibition of the interaction of PD-L1 or PD-1and PD-L2 or the intracellular signalings of PD-1. A substance that selectively binds to PD-1, PD-L1, or PD-L2 respectively is included as a substance with those inhibitory activities. For example, it is suitable to be protein, polypeptide or peptide, polynucleotide or polynucleoside, antibody or the derivative, organic synthesis compound, inorganic compound, or natural product. Especially, an antibody to PD-1, PD-L1 or PD-L2 is enumerated as an excellent substance in specificity.

The immunosuppressive signals are inhibited by inhibiting production of PD-1, PD-L1 or PD-L2 itself.

As an antibody to PD-1, PD-L1 or PD-L2, all antibodies derived from human, mouse, rat, rabbit, or goat which can inhibit the immunosuppressive signals by PD-1, PD-L1, or PD-L2, those polyclonal or monoclonal antibodies, complete or shorten (for example, F(ab')2, Fab', Fab, or Fv fragment) antibodies, chimeric antibodies, humanized antibodies, or completely humanized antibodies will be acceptable.

Such antibodies can be manufactured using a partial protein of the extracellular region of PD-1, PD-L1, or PD-L2 as an antigen according to well-known production methods of antibody or antiserum. The partial protein of the extracellular region can be prepared by well-known protein expression and purification techniques.

The polyclonal antibodies can be manufactured according to well-known methods. For example, they can be manufactured by separation and refinement of the antibody of which a mixture of an antigen and a carrier protein is immunized to suitable animal, and an antibody inclusion to the antigen is gathered from the immunized animal. As such animal, mouse, rat, sheep, goat, rabbit, and guinea pig are generally enumerated. To improve the antibody producibility, Freund's complete adjuvant or Freund's incomplete adjuvant can be administered with the antigen. The administering is usually executed once every two weeks about 3-10 times in total. The polyclonal antibody can be gathered from the immunized animal's blood and peritoneal fluid, etc. by the above method. The measurement of the polyclonal antibody's titer in antiserum can be measured by ELISA. The separation and refinement of the polyclonal antibody can be executed by refining techniques that use active adsorbents such as antigen binding solid phase, protein A, or protein G, etc., salting-out, alcohol precipitation, isoelectric precipitation, electrophoresis, adsorption and desorption with ion exchanger, uitracentrifugation, or separation and refinement of immunoglobulins such as gel filtration technique, etc.

As an antibody preparation, the monoclonal antibody or the modifier is more suitable.

The monoclonal antibody producing cells can be prepared as hybridomas to be possible to subculture which produce the monoclonal antibody by selecting the individual of which the antibody titre is confirmed in an antigen immunized animals, gathering the spleen or the lymph node on day 2-5 after the final immunization, and fusing the antibody producing cells included in them with homogeneous or heterozoic myeloma cells. The antigen itself or with the carrier and the diluent is administered to the part in which the antibody production is possible. To improve the antibody producibility, Freund's complete adjuvant or Freund's incomplete adjuvant can be administered with the antigen, According to the method of calling "DNA Immunization", animals are immunized. This method is a method using a phenomenon in which antigen-expressing vectors are introduced into the part and are taken into myocytes on the process of tissue repair, and expresses the antigenic protein (*Nature Immunology* (2001), vol. 2, Issue 3, p. 281-267) after Cardiotoxin is treated to immune animal's tibialis anterior muscle of hind leg.

As an immune animal, mouse, rat, sheep, goat, rabbit, or guinea pig can be used, mouse and rat are suitable. The fusion operation can be executed by the method (*Nature* (1975), vol. 256, issue 5517, p. 495-497) of Kohler and Milstein, and as fusion accelerants, polyethylene glycol (PEG) and Sendai virus, etc. are used. As those myeloma cells, myeloma cells such asP3U1, NS1, SP2/0, and AP1 can be used, P3U1 are often used usually. The monoclonal antibody producing cells can be selected by detecting by ELISA, etc. executed by adding hybridoma culture supernatant to solid phase in which antigenic proteins are adsorbed direct or with carrier perhaps. Hybridoma culture supernatant's antibody titre can be measured by ELISA. The separation and refinement of the monoclonal antibody can be executed according to the separation refining method similar to the separation and refinement of immunoglobulin for the above polyclonal antibody. Concretely, it is anti-mouse PD-L1 antibody producted by hybridomas identified by International Trust Number FERM BP-8396 or anti-human PD-1 antibody producted by a hybridoma identified by International Trust Number FERM BP-8392.

The hybridomas identified by International Trust Number FERM BP-8392 had been deposited as Trust Number FERM P-19162 to National Institute of Advanced Industrial Science and Technology, International Patent Organism Depositary in Central 6, 1-1-1 Higashi, Tsukuba, Ibaraki, Japan (ZIP code 305-8566) at Dec. 19, 2002, and had been transferred to International Deposit at Jun. 5, 2003. The hybridomas identified by International Trust Number FERM BP-8396 had been deposited as Trust Number FERM P-18908 at Jun. 25, 2002, and had been transferred to International Deposit at Jun. 11, 2003.

The antibody fragment means $F(ab')_2$, Fab', Fab, or scFv antibody fragment and can be prepared by reducing optionally after processing with protease enzyme.

$F(ab')_2$ antibody fragments can be purified by either method of affinity chromatography such as ion-exchange chromatography, gel filtration, or protein A or protein G column, etc, after the purified monoclonal antibody is completely digested by pepsin. Because digestive time by pepsin is different depending on Ig subtype, it is necessary to prepare it suitably. Fab' antibody fragment can be prepared by reducing $F(ab')_2$ by 2-mercaptoethylamine partly. Fab antibody fragment can be prepared by the direct digestion under the presence of cysteine by the digestive enzyme papain followed by refining.

Further, the monoclonal antibody is prepared as a rearrangement antibody and a hybrid antibody modified by gene recombination technology using DNA sequence that codes the amino acid sequence of antibody isolated from the hybridomas. For example, it can be prepared as a single-chain antibody but not a usual complete type antibody. scFv antibody (single chain Fv) can be prepared by the method of Jost (*Journal of Biological Chemistry* (1994), vol. 269, issue 42, p. 26267-26273). The single-chain antibody with the characteristic and the affinity of an original antibody can be prepared by making expression an expression vector including a fused DNA of which DNA fragments respectively coding a variable region of the heavy chain and the light chain had been connected with a spacer coding neurtal amino acids (glycine or serine) in suitable host cells.

When non-human antibody is used to treat for human, it is indispensable to decrease the antigenicity of the antibody. Since the immune reaction to patient's antibody often shortens an effective treatment period, the process of decreasing the antigenicity of the antibody by making the antibody humanize or completely human type is necessary. The humanized antibody modified to be acceptable for administering to human is the antibody which is modified so that the decrease of antigenicity or the blood movement may improve to extent that can be allowed in pharmacology when the antibody is administered to human.

Human PD-1 antibody or human PD-L1 antibody in specification of the present invention includes the humanized or the complete human type antibody, too.

The humanized antibody can be prepared by substituting a part of non-human antibody which was prepared by being immunized to mammals other than human for a part of human antibody. Concretely, it has been known to be able to be prepared by constructing a chimera with a gene coding a constant region of the human antibody (*Proc. Natl. Acad. Sci.* (USA) (1987), vol. 84, p. 3439-3443, *Journal of Immunology* (1987), vol. 139, issue 1, p. 3521). The DNA sequence of the human constant region has been described to a prior art and the constant region gene can be easily obtained from an already-known clone. Then, the DNA sequence coding the variable region of the antibody can be fused to the human constant region. An isotype of the human constant region can be selected due to desire effective function or antibody dependent cytotoxicity. A suitable isotype is IgG1, IgG3, and IgG4. Both human light-chain constant region, κ chain, and λ chain can be used. It is possible to make this humanized chimeric antibody expression by a routine method.

The complete human type antibody can be prepared by using mice (XenoMouse (*Chemical Biology* (2000), vol. 7, issue 8, p. R185-6), HuMAb-Mouse (*Infection and Immunity* (2002), vol. 70, issue 2, p. 612-9), TC mouse (*Biotechnology and Genetics Enginnering Revew* (2002), vol. 19, p. 73-82), and KM mouse (*Cloning Stem Cells* (2002), vol. 4, issue 1, p. 91-102)) of which a constant region gene of human immunoglobulin have been transferred, and a target antibody can be mass-produced by making the antibody production lymphocytes separated from mice to hybridomas. It can be prepared by phage display method (*FEBS Letter* (1998), vol. 441, p. 20-24). In this method, by using phages of which the human antibody gene have been incorporated into a cyclic single strand DNA, the human type antibody can be expressed on the surface of the phage as a form fused with coat protein of the phages.

Polypeptides or the derivatives that bind to PD-1, PD-L1, or PD-L2 include each partial proteins of PD-1, PD-L1 or PD-L2 of which the immunosuppressive signal is not induced. The presence of PD-1 in the neighborhood of the antigen receptors is indispensable for the inducement of the immunosuppressive signal of PD-1, for that purpose it is necessary to be restrained by the interaction with PD-L1 or PD-L2 in antigen-presenting cells, tumours, or carcinoma calls. Therefore, soluble PD-L1 or soluble PD-L2 with a part which is only extracellular domains and interacts with PD-1 can inhibit the immunosuppressive signal of PD-1. On the other hand, soluble PD-1 with a part which has a similar structure and can interact with PD-L1 or PD-L2 can inhibit the immunosuppressive signal. These soluble proteins have only to include an extracellular region which is necessary and sufficient to bind to PD-1, PD-L1, or PD-L2 and can be prepared by a well-known expression and refining technique.

If an interaction inhibitor of PD-1 and PD-L1 or PD-1 and PD-L2 is a protein or a polypeptide and an essential area for the interaction is composed by only consecutive polypeptide, such a polypeptide fragment can become a mutual antagonist. Further, an antagonist with stronger activity can be identified from molecular groups of which this polypeptide fragment is chemically modified, or designed by computer based on the spatial structure of the polypeptide fragment. Also, the best antagonist can be more efficiently selected from molecular groups designed by computer based on protein stereoanalysis data of the interaction area.

A substance that inhibits the interaction of PD-1 and PD-L1, or PD-1 and PD-L2 can be screened directly. Such a substance can be identified from each libraries of protein, polypeptide or peptide, polynucleotide or polynucleoside, non-peptide compound, organic synthesis compound, or natural product (for example, fermentational product, cell extract, plant extract, and animal tissue extract).

Since the inhibitory signals of PD-1 intracellular domain are caused by contacting dephosphorylation enzymes (for example, SHP-1 and 2 (Sathish J G, *Journal of Immunology* (2001), vol. 166, issue 3, p. 1763-70)) that bind to ITIM in PD-1intracellular domain with an intracellular complex including an antigen receptor complex, they are generally inhibited by inhibiting the contact between the antigen receptor complex and PD-1. The substance that inhibits the inhibitory signals includes a substance that directly inhibits the activity of dephosphorylation enzymes, a substance that inhibit phosphorylation of tyrosine residue in ITIM, a substance that inhibits bonds of dephosphorylation enzymes to ITIM, or a substance that directly inhibits activity of dephosphorylation enzymes, etc. The antigen receptor complex includes T cell receptor complex or B cell receptor complex.

The production of PD-1, PD-L1, or PD-L2 is inhibited by specific polynucleotide or polynucleoside, organic synthesis compound, inorganic compound, or natural product, etc. Especially, the suitable polynucleotide or polynucleoside includes antisense nucleotide derivative so-called ribozyme. This uses a mechanism of which the expressed mRNA is destroyed by which the polynucleotide derivative that is complement to mRNA of PD-1, PD-L1, or PD-L2 is transferred into subject cells. Further, the vector can be used for the gene manipulation to lymphocyte stem cells gathered from a patient so that it inhibits the expression of PD-1, and the manipulated cells can be used for cell medical treatment of which the cells will be proliferated, differentiated, activated, and administered to the patient again. Especially, in immunotherapy for cancer, more specific and clonal lymphocytes to target cells can be prepared by adding a specific antigen of the target cells on the process of the maturation and activation of lymphocyte stem cells.

The screening method of the present invention can be executed by a method of measuring cell function. The carcinoma cell lines for screening of which PD-L1 or PD-L2 used by the method is transformed to be expressed includes carcinoma cell lines transformed transitory or stably after expression vectors constructed to express PD-L1 or PD-L2 have been introduced to the cells by well-known methods. As the carcinoma cell lines used, ape COS-1 cells, COS-7 cells, Vero, chinese hamster CHO cells (hereafter, abbreviated with CHO cells), dhfr gene deficient chinese hamster CHO cells (hereafter, abbreviated with CHO (dhfr-) cells), mouse L cells, mouse AtT-20, mouse myeloma cells, rat GH3, HEK293 T cells, and human FL cells, etc. are used. Especially, the transformation of animal cells can be executed according to methods described in, for example, *Cell Tehcnology* separate volume 8, *New Experimental Protocol of Cell Technology* (1995), vol. 263, published by SHUJUNSHA Co., Ltd., and Virology (1973), vol. 52, issue 456.

Cells naturally expressing PD-L1 or PD-L2 can be also used. Such cells include leukocyte, suitablely, monocytes, macrophages or antigen-presenting cells, epithelial cells, tumor cells, carcinoma cells, or those cell lines, etc. As tumor cells or carcinoma cells, for example, P38D1 cells, P815 cells, NB41A3 cells, MDA-231 cells, SKBR-3 cells, MCF-7 cells, BT474 cells, J558L cells, P3U1 cells, PAI cells, X63 cells, or SP2/0 cells can be used. Cells infected with pathogens, which express PD-L1 or PD-L2 naturally or compellingly, can be used, infectious pathogens include human hepatitis virus (hepatitis B, hepatitis C, and hepatitis A) or hepatitis E), human retrovirus, human immunodeficiency virus (HTLV1 and HIV2), human T cell leukemia virus, human T lymphocytic virus (HTLV1 and HTLV2), simple herpes virus type 1 or 2, Epstein-Barr virus, cytomegalovirus, varicella-zoster virus, human herpesvirus including human herpesvirus 6, poliovirus, measles virus, rubella virus, Japanese encephalitis virus, mumps virus, influenza virus, adenovirus, enterovirus, rhinovirus, virus developing severely acute respiratory syndrome (SARS), Ebola virus, West Nile virus, or these virus modified artificially. Other pathogens include, for example, pathogenesis protozoan (for example, trypanosome, malaria, and toxoplasma), bacillus (for example, mycobacterium, salmonella, and listeria) or fungus (for example, candida), etc.

The lymphocytes used in the screening method of the present invention are T or B lymphocytes, and suitably cytotoxic T lymphocytes (CTL). The immune reaction of lymphocytes in the screening method of the present invention includes citotoxic response (for example, tumor immunity reaction), mixed lymphocyte reaction, production of cytokines, antibodies, complements or other cell surface antigens, or cellular proliferation, etc.

In the present invention, the screening method of an active ingredient contained in the composition for immunopotentiation or cancer treatment can be executed by measuring cytotoxic activity of cytotoxic T lymphocytes against subject cells followed by measuring an effect of a subject substance against the activity. This method is an assay of recovery and reinforcement of cytotoxic activity by adding the subject substance to a culture mixed cytotoxic T lymphocytes (CTL) naturally expressing PD-1 or cell lines (for example, 2C cells) with cells naturally or compulsorily expressing PD-L1 or PD-L2 which are derived from syngeneic mouse. Since the cytotoxic activity against PD-L1 or PD-L2 expressing cells is lower than that against PD-L1 or PD-L2 non-expressing cells, this method has a feature of which the recovery of cytotoxic activity (rising part) due to the subject substance can be measured more clearly. The recovery of cytotoxicity due to the subject substance can be evaluated as an equivalent to inhibition of suppression of cytotoxicity. Further, it is preferable that the the cytotoxicity due to the subject substance is arbitrarily measured. As these cells, tumor cell lines or carcinoma cell lines naturally expressing PD-L1 or PD-L2 (*Nature Immunology* (2001), vol. 2, issue 3, p. 261-267), for example, P38D1 cells, P815 cells, NB41A3 cells, MDA-231 cells, SKBR-3 cells, MCF-7 cells, BT474 cells, J558 L cells, P3U1 cells, PAI cells, X63 cells, or SP2/0 cells can be used, and tumor cell lines or carcinoma cell lines transformed so as to stably or transiently express PD-L1 or PD-L2can be also used.

On the other hand, it is preferable that the cytotoxic lymphocytes are PD-1expressing cells derived from syngeneic animal to targeted cells.

In the present invention, the screening method of an active ingredient contained in the composition for infection treatment is an assay of enhancement effect on immune reaction of lymphocytes to infected cells or inhibitory effect on proliferation activity of pathogen or virus by adding the subject substance to a culture mixed cytotoxic T lymphocytes (CTL) or cell lines (for example, 2C cells) naturally expressing PD-1 with cells naturally or compulsorily expressing PD-L1 or PD-L2 which are derived from syngeneic mouse and was infected with pathogen or virus.

Further, in evaluations using a similar principle, a mammal created by transplanting the above carcinoma cell lines for screening which are transformed so as to express PD-L1 or PD-L2 or cells naturally expressing PD-L1 or PD-L2 to a syngeneic mammal can be used. To a manufacture method of the mammal, a process of transplanting cells and a process of breeding the mammal until becoming appropriate for the evaluation is indispensable. This evaluation is characterized in evaluating proliferation of the transplant cells and the amount of production of various cytokines or cell surface antigens, especially, in case of carcinoma cells, proliferation, permeation, or histological analysis of metastasis of the cells, or survival rates of the transplanted mammal. The cellular proliferation can be evaluated as the number of carcinoma cells per unit capacity in case of ascites tumors or blood cancers, or the size or the weight after removing in case of solid cancer. The effect of the subject substance for cancer treatment in this method can be evaluated as an equivalent to effect due to inhibition of suppression of cytotoxicity caused in PD-L1 or PD-L2. As such cells, syngeneic cells to a mammal for transplant, with good proliferation are more suitable. The mammal include s primates except human, mouse, rat, hamster, guinea pig, dog, pig, and ape.

INDUSTRIAL AVAILABILITY

As a substance that demonstrates remarkable suppression of cancer proliferation and life prolongation of an individual by administering to the carcinoma cells-transplanted animal model, the present inventors invented each specific antibody (anti-PD-1antibody and anti-PD-L1 antibody) that inhibited PD-1 and PD-L1 function respectively. These antibodies showed actions that recover or reinforce cytotoxic activity that has relatively decreased by presenting PD-L1 ligand to PD-1-expressing CTL (cytotoxic T lymphocyte) (example 1 and FIG. 1). This suggests that the cytotoxic activity to carcinoma cells by CTL could be reinforced by administering these antibodies. In the carcinoma cells-transplanted animal model (*Protein, Nucleic acid, and Enzyme* (1981), vol. 26, issue 3, p. 208-22) which uses syngeneic mouse of which cell lines artificially expressing PD-L1 derived from mastocytomas have been imported, administration of anti-PD-L1 antibody presented suppression of proliferation, invasion, and metastasis of carcinoma cells, and life prolongation of an individual (FIGS 2 and 3.). It was suggested that inhibition of PD-1 function or production could achieve an effect similar to the effect on inhibition of PD-L1 function by this antibody.

This is based on non-proliferation of imported carcinoma cells in the cancer imported model using PD-1-deficient mice, and presents that inhibition of PD-1 function or production could be effective on cancer treatment (Example 5 and FIG. 3.).

Actually, it had been proven that administration of anti-PD-1 antibody significantly suppressed metastasis of imported carcinoma cells to liver in the cancer imported animal model (Example 13).

The inventors presented that the substance that inhibits the immunosuppressive signal induced by PD-1, PD-L1 or PD-L2 was useful for infection treatment (Example 11, FIGS. 15 and 16).

These results experimentally presented by the present inventors prove that only PD-1 antibody or PD-L1 antibody don't presents aforementioned effect, but also any substance that can inhibit the immunosuppressive signal from PD-1, PD-L1, or PD-L2 present almost similar effect. The substances with such effects include, for example, anti-PD-L2 antibody, soluble PD-1, soluble PD-L1, soluble PD-L2, PD-1 antagonists, PD-L1 antagonists, PD-L2 antagonists, substances that inhibits interaction between PD-1 and PD-L1 or PD-1 and PD-L2, PD-1 production inhibitors, PD-L1 production inhibitors, PD-L2 production inhibitors, and intracellular inhibitory signal inhibitors by PD-1.

Cancer or tumour of which the therapeutic potential could be expected by administration of the composition for cancer treatment of the present invention include, for example, carcinoma, squamous carcinoma (for example, cervical canal, eyelid, tunica conjunctiva, vagina, lung, oral cavity, skin, urinary bladder, tongue, larynx, and gullet), and adenocarcinoma (for example, prostate, small intestine, endometrium, cervical canal, large intestine, lung, pancreas, gullet, intestinum rectum, uterus, stomach, mammary gland, and ovary). Further, they include sarcomata (for example, myogenic sarcoma), leukosis, neuroma, melanoma, and lymphoma.

The effect on the ones that remarkably express PD-L1 or PD-L2 in these cancers or tumours is remarkable. PD-L1 or PD-L2 expression can be identified by checking up surgically excised cancer, tumour mass, or lesioned part gathered outside of the body as a sample. Administration of the composition of the present invention will become an efficient and available method as a treatment after surgery for tumour or cancer patient that PD-L1 or PD-L2 is remarkably expressed, PD-L1 or PD-L2expression can be identified by, for example, immunochemical method using PD-L1antibody or PD-L2 antibody, RT-PCR, or DNA array.

A side reaction violently decreasing lymphocytes proliferation in chemotherapy and radiotherapy for cancer is inevitable. Administration of the composition of the present invention presents an effect on stimulating and proliferating the decreased lymphocytes and can suppress a fierce side reaction accompanied by usual chemotherapy to minimum. Further, it is similar as to radiotherapy. Concomitant use with the composition of the present invention can greatly decrease the dose of chemotherapy drug or the exposure dose of irradiation from the dose or the exposure dose used usually.

The composition for cancer treatment of the present invention can be used together with existing chemotherapy drugs or be made as a mixture with them. Such a chemotherapy drug include, for example, alkylating agents, nitrosourea agents, antimetabolites, antitumor antibiotics, alkaloids derived from plant, topoisomerase inhibitors, hormone therapy medicines, hormone antagonists, aromatase inhibitors, P-glycoprotein inhibitors, platinum complex derivatives, other immunotherapeutic drugs, and other anticancer agents. Further, they can be used together with hypoleukocytosis (neutrophil) medicines that are cancer treatment adjuvant, thrombopenia medicines, antiemetic drugs, and cancer pain medicines for patient's QOL recovery or be made as a mixture with them.

The composition for cancer treatment of the present invention can be used together with immunopotentiative substances or be made as a mixture with them. Such immunopotentiative substances include, for example, various cytokines and a tumor antigen, etc. Cytokines that stimulate immune reactions include, for example, GM-CSF, M-CSF, G-CSF, interferon-$\alpha$, $\beta$, $\gamma$, IL-1, IL-2, IL-3, and IL-12, etc, B7 ligand derivatives, anti-CD3 antibodies and anti-CD28 antibodies, and anti-CTLA-4 antibodies can also improve the immune reactions.

Administration of the tumor antigen can also improve a specific immune reaction against T lymphocytes against carcinoma cells and additionally or synergistically reinforce by using together with the composition for cancer treatment of the present invention. The tumor antigen can be prepared as a purified protein in case of an already-known gene, or as a lysate of carcinoma cells in case of an unknown gene.

Such the tumor antigen includes, for example, HLA-A1 and HLA-A2 restrictive peptides of malignant melanoma MAGE-1 or MAGE-3, MART-1, and gp11. Further, they include HER2/neu peptide of mammary carcinomas and ovarian carcinomas, MUC-1 peptide of adenocarcinoma, and NY-ESO-1 of metastatic carcinomas.

It has been thought that viruses could use conjugate suppressive factors of T lymphocytes as one of methods to escape from host's immuno-protection. It is thought that a part of virus infection could attribute the escape function of such viruses and administration of the composition of the present invention could improve the immune reaction of T lymphocytes to viruses.

Administration of the composition for infection treatment of the present invention is effective on treatment for, for example, human hepatitis virus (hepatitis B, Hepatitis C, hepatitis A, or hepatitis E), human retrovirus, human immunodeficiency virus(HIV1, HIV2), human T leukemia virus (HTLV1, HTLV2), or human lymphocytic cell type virus. Further, it is thought to be effective on treatment for simple herpes virus type 1 or 2, epstein-barr virus, cytomegalovirus, varicella-zoster virus, human herpesvirus including human herpesvirus 6, poliovirus, measles virus, rubella virus, Japanese encephalitis virus, mumps virus, influenza virus, adenovirus, enterovirus, rhinovirus, virus developing severely acute respiratory syndrome (SARS), ebola virus, west nile virus, or these virus modified artificially.

It is thought to be also effective on infection treatment for other pathogens such as, for example, pathogenesis protozoan (for example, trypanosome, malaria, and toxoplasma), bacillus (for example, mycobacterium, salmonella, and listeria) or fungus (for example, candida), etc.

The composition for infection treatment of the present invention can be used together with existing anti-HIV drugs, antiviral agents, antibiotic agents, antimicrobial agents, or visceral mycosis medicines or be made as a mixture with them. The anti-HIV drugs include, for example, reverse transcriptase inhibitors (for example, AZT, ddI, 3TC, and d4T), protease inhibitors (for example, saquinavir mesylate, ritonavir, nelfinavir mesylate, amprenavir, delavirdine mesylate, saquinavir, and lopinavir/ritonavir) or CCR5 receptor antagonists. The antiviral agents include, for example, anti-herpesvirus agents, anti-influenza virus agents, interferon-$\alpha$ and $\beta$, or various immunoglobulins.

The composition for infection treatment of the present invention can be used together with vaccines of virus or pathogen or be made as a formulation with them. Such vaccines include, for example, poliovaccine, measles vaccine, Japanese encephalitis vaccine, BCG vaccine, triple vaccine, mumps virus vaccine, varicella virus vaccine, influenza vaccine, hepatitis A vaccine, hepatitis B vaccine, and cholera vaccine.

The composition of the present invention is usually administered systemically or locally, and orally or parenterally.

The dosage is determined depending on medicines used for the present invention, age, body weight, symptom, therapeutic effect, administration route, and duration of the treatment, etc. For oral administration, generally, the dosage range from 1 μg to 100 mg per an adult is orally administered once to several times per day, or the dosage range from 0.1 ng to 10 mg per an adult is administered once to several times per day parenterally, suitably intravenously, and is intravenously administered for 1 to 24 hours per day continuously.

Since the dosage changes depending on various conditions as described above, there are cases in which doses lower or greater than the above dosage may be used.

When a concomitant drug of the composition of the present invention and other medicines is administered, it is used as solid medicines for internal use, and injections, external preparations, suppositoriums, inhalant, pernasal preparation, etc. for parenteral administration.

The solid medicines for oral administration include compressed tablets, pills, capsules, dispersing powders, granules, etc. The capsules include hard capsules and soft capsules. The tablets include sublingual tablets, intraoral strapping tablets, and intraoral speed disintegrators, etc.

As to such the solid medicines, one or more active compound(s) may be pharmaceutically manufactured as itself/themselves or a formulation with excipients (lactose, mannitol, glucose, microcrystal cellulose, and starch, etc.), binders (hydroxypropylcellulose, polyvinyl pyrrolldone, and magnesium metasilicate aluminate, etc.), disintegrators (cellulose calcium glycolate, etc.), lubricants (magnesium stearate etc.), stabilizers, or solubilizers (glutamate and aspartic acid, etc.), etc. according to usual methods. Further, they may be optionally coated by coatings (sucrose, gelatin, hydroxypropylcellulose, and hydroxypropylmethylcellulose phthalate, etc.) or coated in the layer of two or more. Further, capsules of absorbable materials such as gelatin may be included.

The sublingual tablets are manufactured according to a well-known method. For example, they may be pharmaceutically manufactured as a mixture one or more active compound(s) with excipients (lactose, mannitol, glucose, microcrystal cellulose, colloidal silica, and starch, etc.), binders (hydroxypropylcellulose, polyvinylpyrrolidone, and magnesium metasilicate aluminate, etc.), disintegrator (starch, L-hydroxypropylcellulose, carboxymethylcellulose, crosscarmellose sodium, and cellulose calcium glycolate, etc.), lubricants (magnesium stearate etc.), swelling agents (hydroxypropylcellulose, hydroxypropylmethylcellulose, carbopole, carboxymethylcellulose, polyvinyl alcohol, xanthan gum, and Cyamoposis Gum, etc.), swelling adjuvants (glucose, fructose, mannitol, xylitol, erythritol, maltose, trehalose, phosphate salt, citrate, silicate, glycine, glutamate, and arginine, etc.), stabilizers, solubilizers (polyethylene glycol, propylene glycol, glutamate, and aspartic acid, etc.), or spices (orange, strawberry, mint, lemon, and vanilla, etc.), etc. according to usual methods. Further, they may be optionally coated by coatings (sucrose, gelatin, hydroxypropylcellulose, and hydroxypropylmethylcellulose phthalate, etc.) or coated in the layer of two or more. Additives such as preservatives, anti-oxidants, coloring agents, and sweeteners used regularly may be optionally added.

The intraoral strapping tablets are manufactured according to a well-known method. For example, they may be pharmaceutically manufactured as a mixture one or more active compound(s) with excipients (lactose, mannitol, glucose, micocrystal cellulose, colloidal silica, and starch, etc.), binders (hydroxypropylcellulose, polyvinylpyrrolidone, and magnesium metasilicate aluminate, etc.), disintegrator (starch, L-hydroxypropylcellulose, carboxymethylcellulose, crosscarmellose sodium, and cellulose calcium glycolate, etc.), lubricants (magnesium stearate etc.), swelling agents (hydroxypropylcellulose, hydroxypropylmethytcellulose, carbopole, carboxymethylcellulose, polyvinyl alcohol, xanthan gum, and Cyamoposis Gum, etc.), swelling adjuvants (glucose, fructose, mannitol, xylitol, erythritol, maltose, trehalose, phosphate salt, citrate, silicate, glycine, glutamate, and arginine, etc.), stabilizers, solubilizers (polyethylene glycol, propylene glycol, glutamate, and aspartic acid, etc.), or spices (orange, strawberry, mint, lemon, and vanilla, etc.), etc. according to usual methods. Further, they may be optionally coated by coatings (sucrose, gelatin, hydroxypropylcellulose, and hydroxypropylmethylcellulose phthalate, etc.) or coated in the layer of two or more. Additives such as preservatives, anti-oxidants, coloring agents, and sweeteners used regularly may be optionally added.

The intraoral speed disintegrators are manufactured according to a well-known method. For example, they may be pharmaceutically manufactured as one or more active compound(s) itself/themselves or a mixture bulk or granulated bulk particle with suitable coatings (ethyl cellulose, hydroxypropylcellulose, hydroxypropylmethylcellulose, and acrylic acid methacrylate copolymer, etc.). plasticizers (polyethylene glycol and triethyl citrate, etc.), excipients (lactose, mannitol, glucose, crystallite cellulose, colloidal silica, and starch, etc.), binders (hydroxypropylcullulose, polyvinyl pyrrolidone, and magnesium metaslicate aluminate, etc.), disintegrators (starch, L-hydroxypropylcellulose, carboxymethylcellulose, crosscarmellose sodium, and cellulose calcium glycolate, etc.), lubricants (magnesium stearate etc.), dispersant adjuvants (glucose, fructose, mannitol, xylitol, erythritol, maltose, trehalose, phosphate salt, citrate, silicate, glycine, glutamate, and arginine, etc.), stabilizers, solubilizer (polyethylene glycol, propylene glycol, glutamate, and aspartic acid, etc.), spices (orange, Strawberry, Mint, lemon, and vanilla, etc.) etc. according to usual methods. Further, they may be optionally coated by coatings (sucrose, gelatin, hydroxypropylcellulose, and hydroxypropylmethylcellulose phthalate, etc.) or coated in the layer of two or more. Additives such as preservatives, anti-oxidants, coloring agents, and sweeteners used regularly may be optionally added.

The liquid compositions for oral administration include pharmaceutically acceptable wafers, suspensions, emulsions, syrups, and elixirs, etc. As to such liquid medicines, one or more active compound(s) may be dissolved, suspended, or emulsified to generally used diluent (purified water, ethanol or those mixing liquids, etc.). Further, those liquid medicines may contain humectants, suspending agents, emulsifying agents, sweeteners, flavor agents, flavoring agents, preservatives, and buffers, etc.

The external preparations for parenteral administration include, for example, ointments, gels, creams, fomentations, patchs, embrocations, aerosols, inhalants, sprays, aerosols, eye drops, and nasal drops, etc. These include one or more activator(s) and are manufactured by a well-known method or the formula usually used.

The ointments include one or more activator(s) and are manufactured by a well-known method or the formula usually used. For example, they are manufactured by levigating and melting one or more activator(s) to basis.

The ointment bases are chosen from a well-known or the one usually used. They are used mixing one or two or more kinds chosen from, for example, higher fatty acid or higher fatty acid ester (adipic acid, myristic acid, palmitic acid, stearic acid, oleic acid, adipic acid ester, myristic acid ester, palmitate, stearic acid ester, and oleic acid ester, etc.), rows (yellow wax, spermaceti, and ceresin, etc.), surfactants (polyoxyethylene alkyl ether phosphate etc.), higher alcohols (cetanol, stearyl alcohol, and cetostearyl alcohol, etc.), silicone oils (dimethylpolysiloxane etc.), hydrocarbons (hydrophillc petrolatum, white petrolatum, purified lanolin, and liquid paraffin, etc.), glycols (ethylene glycol, diethylene glycol, propylene glycol, polyethylene glycol, and macrogol, etc.), vegetable oils (castor oil, olive oil, sesame oil, and oil of turpentine, etc.), animal oils (mink oil, yolk oil, squalane, and squalene, etc.), water, absorption enhancer, and poisoned inhibitor. Further, they may include moisturizing agents, preservatives, stabilizing agents, anti-oxidants, and flavors, etc.

The gels are manufactured by a well-known method or a formula usually used. For example, they are manufactured by levigating and melting one or more activator(s) to a basis. The base is chosen from a well-known or the one usually used. It is used mixing one or two or more kinds chosen from, for example, lower alcohols (ethanol and isopropyl alcohol, etc.), gelatinizers (carboxymethylcellulose, hydroxyethyl cellulose, hydroxypropylcellulose, and ethyl cellulose, etc.), neutralizers (triethanolamine and diisopropanolamine, etc.), surfactants (mono stearic acid polyethylene glycol, etc.), gums, water, absorption enhancers, and poisoned inhibitors. Further, they may include preservatives, anti-oxidants, and flavors, etc.

The creams are manufactured by a well-known method or a formula usually used. For example, they are manufactured by levigating one or more activator(s) to a basis and spreading and rolling on the support after kneading. The base is chosen from a well-known or the one usually used. It is used mixing one or two or more kinds chosen from, for example, higher fatty acid esters, lower alcohols, hydrocarbons, polyhydric alcohols (propylene glycol, 1,3-butylene glycol, etc.), higher alcohols (2-hexyl decanol and cetanol, etc.), and emulsifiers (polyoxyethylene alkyl ethers and fatty acid esters, etc.), water, absorption enhancers, and poisoned inhibitors. Further, they may include preservatives, anti-oxidants, and flavors, etc.

The fomentations are manufactured by a well-known method or a formula usually used. For example, they are manufactured by levigating one or more activator(s) to a basis and spreading and rolling on the support after kneading. The base is chosen from a well-known or the one usually used. It is used mixing one or two or more kinds chosen from, for example, thickeners (polyacrylic acid, polyvinyl pyrrolidone, arabic gum, starch, gelatin, and methyl cellulose, etc.), humectants (urea, glycerin, and propylene glycol, etc.), and fillers (china clay, flower of zinc, talc, calcium, and magnesium, etc.), water, absorption enhancers, and poisoned inhibitors. Further, they may include preservatives, anti-oxidants, and flavors, etc.

The patchs are manufactured by a well-known method or a formula usually used. For example, they are manufactured by levigating one or more activator(s) to a basis and spreading and rolling on the support after kneading. The base for the pacth is chosen from a well-known or the one usually used. It is used mixing one or two or more kinds chosen from, for example, high molecular basis, oils, fats, higher fatty acids, tackifiers, and poisoned inhibitors. Further, they include preservatives, anti-oxidants, and flavors, etc.

The liniments are manufactured by a well-known method or a formula usually used. For example, they are manufactured by dissolving, suspending, or emulsifying one or more activator(s) to one or two or more kinds chosen from water, alcohols (ethanol and polyethylene glycol, etc.), higher fatty acids, glycerins, soaps, emulsifiers, suspending agents, etc. Further, they may include preservatives, anti-oxidants, and flavors, etc.

The aerosols, the inhalants, and the sprays may contain stabilizers such as sodium hydrogen sulfite besides the diluent generally used, buffers giving isotonicity, and isotonic agents such as, for example, sodium chloride, sodium citrate, and citrates.

The injections for parenteral administration include solid shots that are dissolved or suspended to solution, suspension, emulsion, or time of use solvent. The injections are used by dissolving, levigating and melting one or more activator(s) to the solvent. As the solvent, for example, water for injection, distilled saline, vegetable oil, propylene glycol, polyethylene glycol, alcohols such as ethanol, etc., and these combination are used. Further, this injection may include stabilizers, solubillzers (glutamate, aspartic acid, and polysorbate 80 (registered trademark), etc.), suspending agents, emulsifying agents, soothing agents, buffers, and preservatives, etc. These are sterilize in the final process or are manufactured from the aseptic manipulation. Aseptic solid medicines may be manufactured as a freeze-drying product and may be used by making to be aseptic or dissolving to aseptic distilled water for injection or other solvents before use.

The inhalant for parenteral administration includes aerosols, inhalant powders, or inhalant solutions, which may be used by making to dissolve or suspend to water or other suitable media at the time of use.

These inhalants are manufactured according to a well-known method.

For example, the inhalant solutions are prepared by properly selecting from preservatives (benzalkonium chloride and paraben, etc.), coloring agent, buffers (sodium phosphate and sodium acetate, etc.), tonicity agents (sodium chloride and concentrated glycerin, etc.), thickeners (carboxyvinyl polymer, etc.), and absorption enhancers, etc., optionally.

The inhalant powders are prepared by properly selecting from lubricants (stearic acid and the salt, etc.), binders (starch and dextrin, etc.), excipients (lactose and cellulose, etc.), coloring agents, preservatives (benzalkonium chloride and paraben, etc.), and absorption enhancers, etc., optionally.

When the inhalant solution is administered, a sprayer (atomizer and nebulizer) is usually used. When the inhalant powder is administered, an inhalation administering machine for powder is usually used.

Other compositions for parenteral administration contain one or more activator(s) and include suppository for intrarectal administration which is prescribed according to a routine procedure and pessary, etc. for intravaginal administering.

The sprays may contain a stabilizer such as sodium hydrogen sulfite besides the diluent generally used, a buffer giving isotonicity, and an isotonic medicine such as, for example, sodium chloride, sodium citrate, or citrates. Production methods of the sprays have been described in, for example, U.S. Pat. No. 2,868,691 specification and U.S. Pat. No. 3,095,355 specification in detail.

BRIEF DESCRIPTION OF DRAWINGS

FIG. 1 (A) shows a flow cytometry that presents PD-1 expression in H-2L$^d$-specific 2C CTL clone and PD-L1 expression of P815 (cell line derived from mastocytoma) stable transfectant clone, and (B) shows a cytotoxic activity of 2C CTL cell line to PD-L1-expressing P815 cell lines and the effect on the cytotoxic activity of anti-PD-L1 antibody (anti-PD-L1 F(ab')$_2$ IgG).

FIG. 2 shows tumor growth and infiltrating of PD-L1-expressing P815 cell lines transplanted into syngeneic mouse. (A) shows the tumour volume (upper) of the transplanted PD-L1-expressing P815 tumours and the survival rate (under) after the transplant, (B) shows the tissue staining view of the transplanted PD-L1-expressing P815 tumour mass in syngeneic DBA/2 mouse (a shows a view (×40) that presents invasion of tumor cells across the abdominal wall and the peritoneum, b shows the same view (×400), c shows the view of invasion into spleen, and d shows the view of invasion into liver.).

FIG. 3 shows in vivo effect of anti-PD-L1 antibody for the tumor growth of the transplanted PD-L1-expressing P815 cell lines in syngeneic mice. (A) shows in vivo effect of anti-PD-L1 antibody for IFN-y production from the tumor-specific CD8+ T cells in mice, (B) shows in vivo effect of anti-PD-L1 antibody for the tumour volume (upper) and the survival rate (under) of the transplanted PD-L1-expressing P815 tumors in mice (squares show control group (rat IgG administrated group) and circles show anti-PD-L1 antibody (anti-PD-L1 F(ab')$_2$ IgG) administrated group in the figure).

Figure 4:
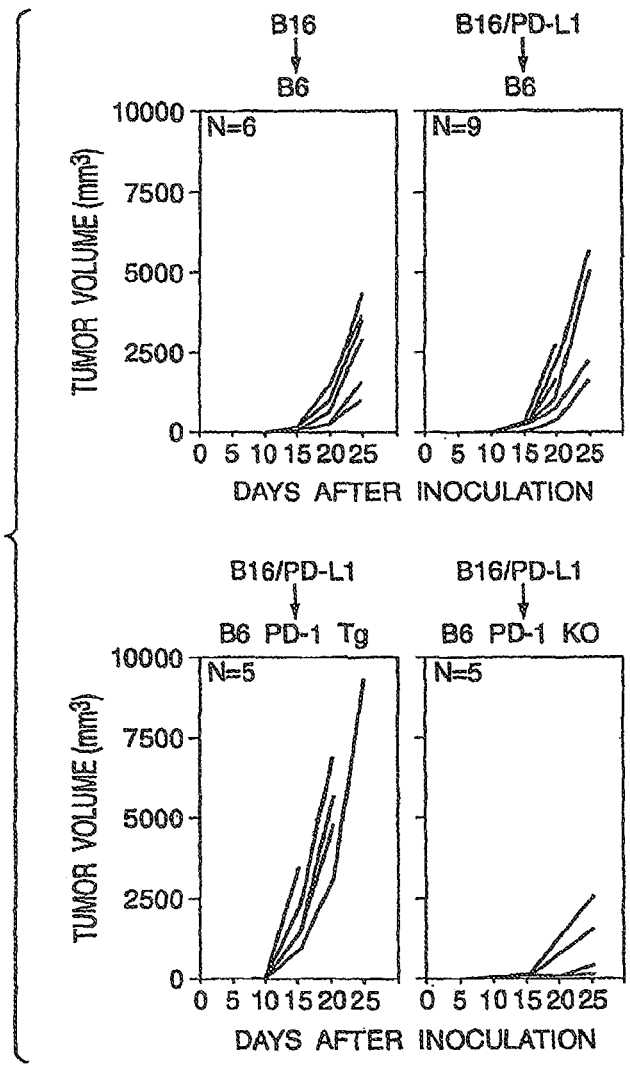

FIG. 4 shows proliferation suppression of PD-L1-expressing B16 melanomas in homo-deficient syngeneic mice (PD-1 −/−).

Figure 5:
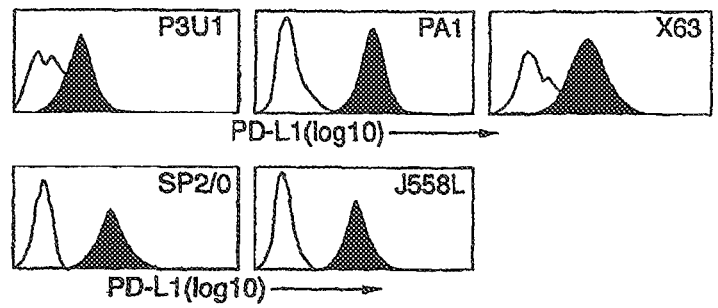
Figure 5:
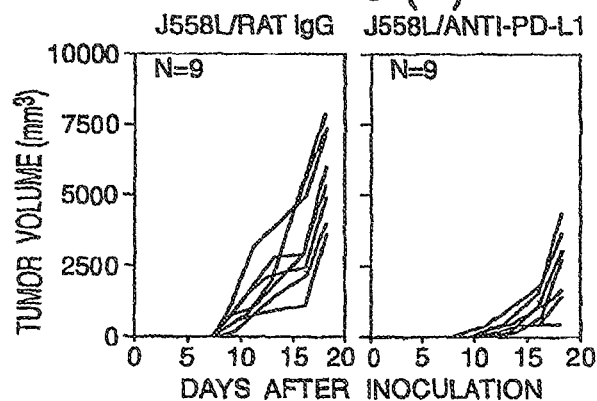
Figure 5:
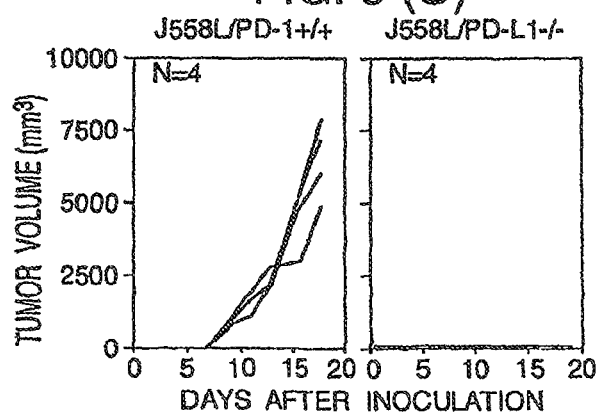

FIG. 5 shows in vivo effect of anti-PD-L1 antibody to tumor growth of transplanted myeloma cell lines in syngeneic mouse (BALB/c) and the involvement of PD-1. (A) shows a flow cytometry that shows PD-L1 expression in various myeloma cell lines, (B) shows in vivo effect of anti-PD-L1 antibody for tumor growth of J558L tumors transplanted in the above mouse, and (C) shows comparison of tumor growth of J558L tumors transplanted in wild type and PD-1 gene deficient (PD-1−/−) syngeneic mice.

Figure 6:
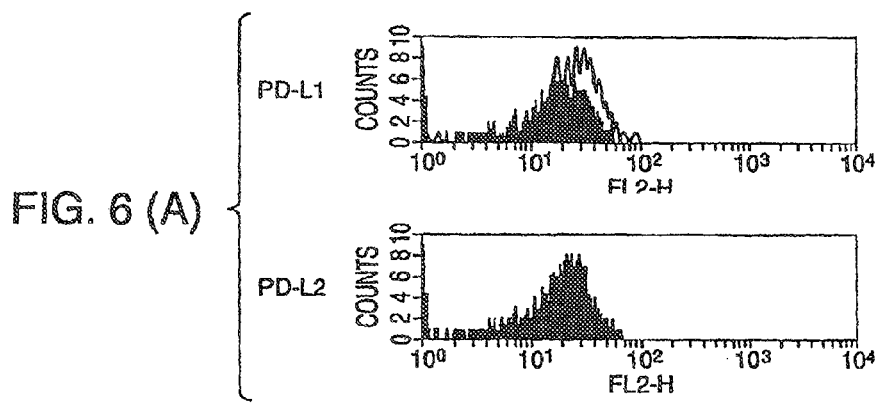
Figure 6:
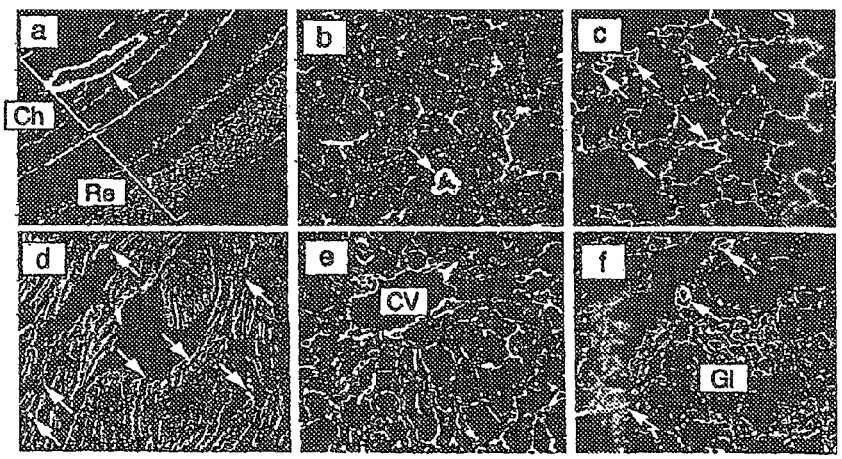

FIG. 6 shows PD-L1 expression in capillary endothelium. (A) shows PD-L1and PD-L2 expression in vascular endothelial cells of mice heart. (B) shows tissue staining of PD-L1 expression in each tissue of mice. Each PD-L1 expression in (a): eyeball, (b): submandibular gland, (c): heart, (d): lungs, (e); liver, (f): kidney is shown. In the figure, Ch means choroidea, CV means middle cardiac vein, Gl means glomerule, and Re means retina. Each arrow shows vascular endothelial cells. Each staining image is enlargement view (×40).

Figure 7:
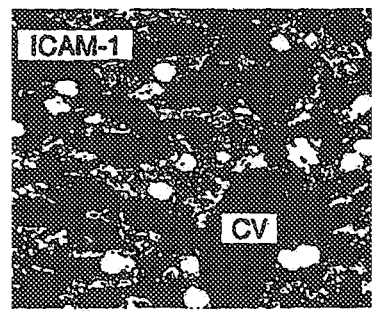
Figure 7:
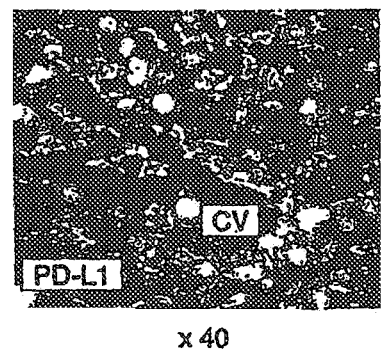

FIG. 7 shows PD-L1 expression in liver non-parenchymal cells.

Figure 8:
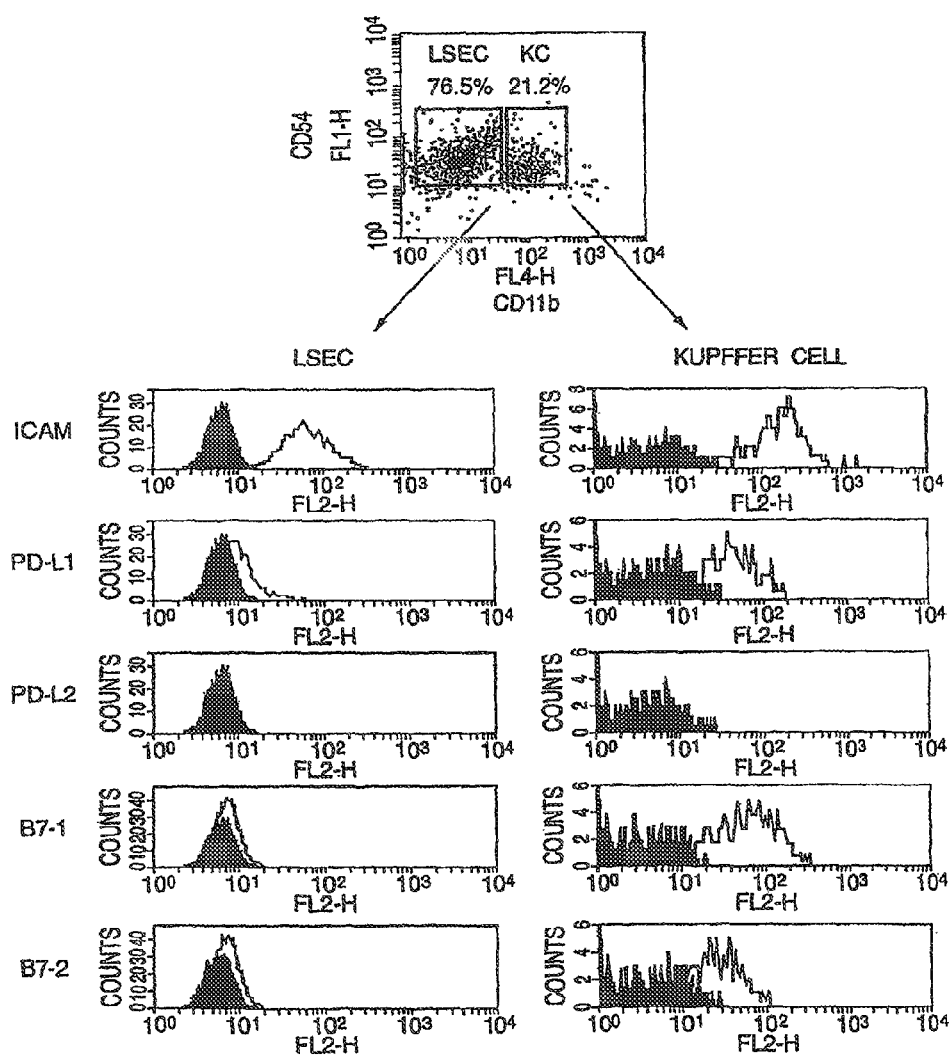

FIG. 8 shows cell surface molecule phenotype in Kupffer cells and liver sinusoidal endothelial cells (LSECs).

Figure 9:
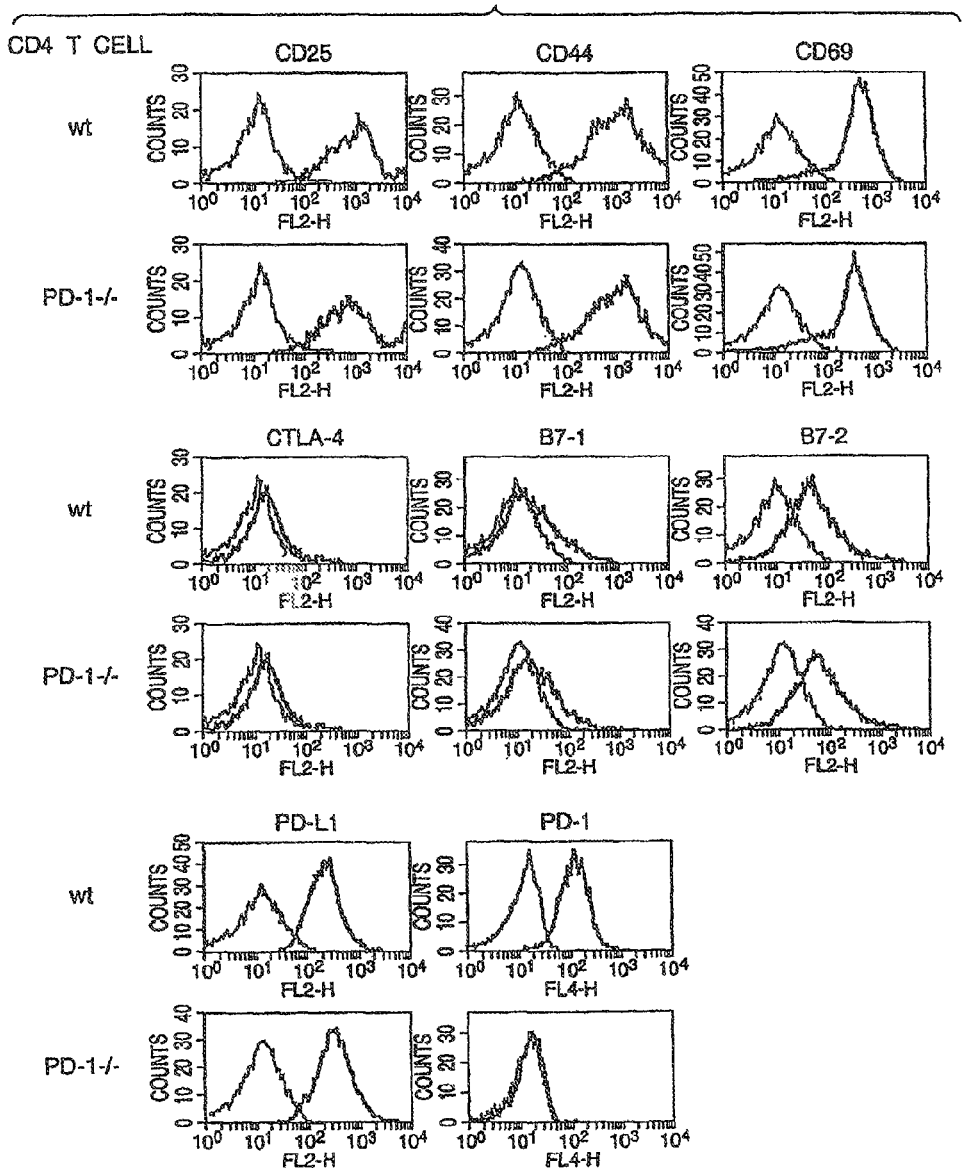

FIG. 9 shows cell surface molecule phenotype in CD4 positive T cells of PD-1 gene homo-deficient mice (PD-1 −/−) or wild type mice (wt).

Figure 10:
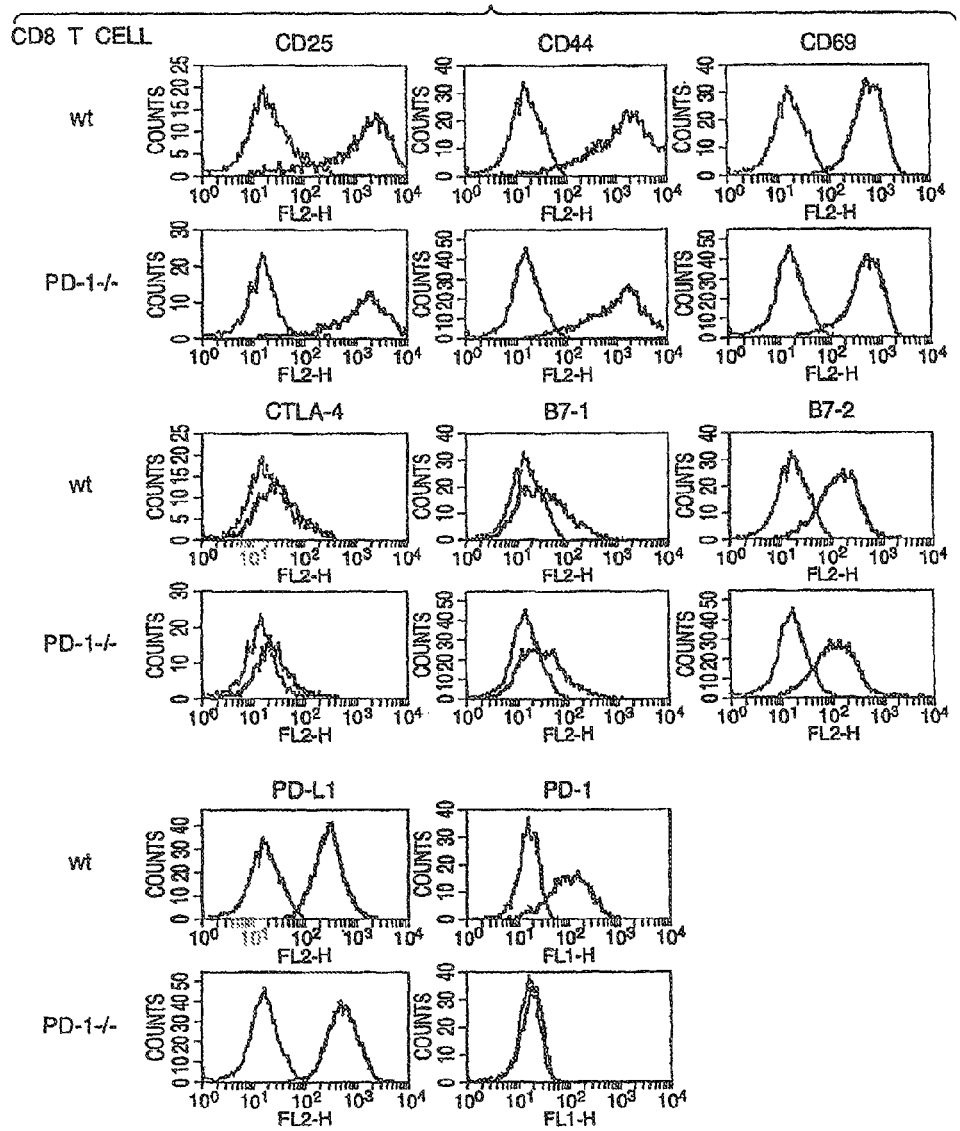

FIG. 10 shows cell surface molecule phenotype in CD8 positive T cells of PD-1 gene homo-deficient mice (PD-1 −/−) or wild type mice (wt).

Figure 11:
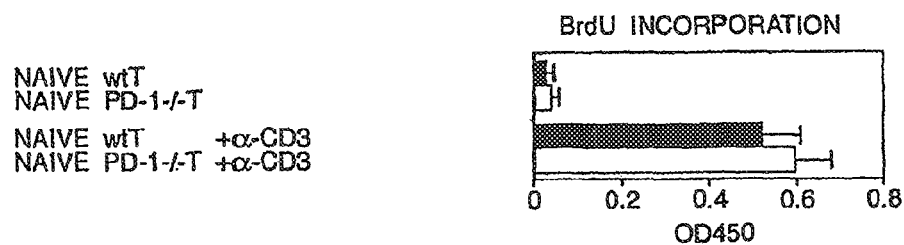
Figure 11:
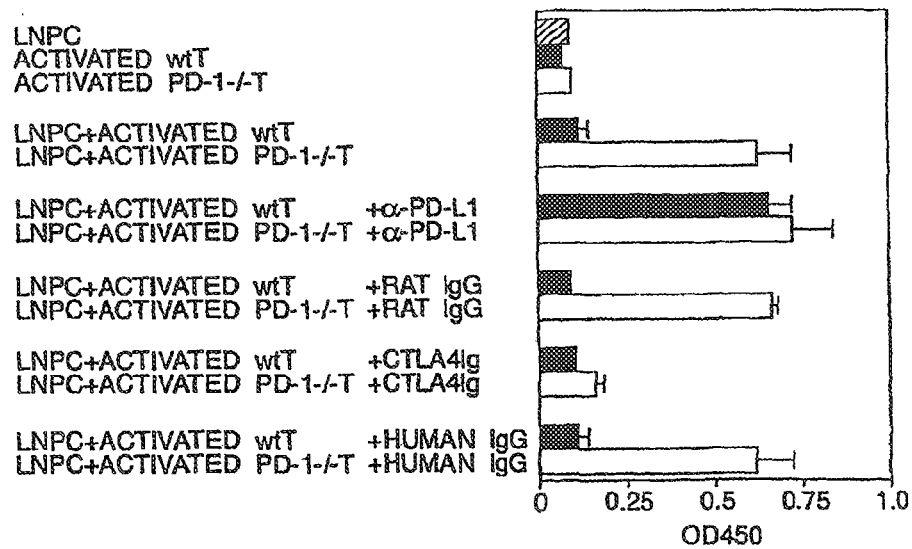

FIG. 11 shows the effect of PD-L1 on T-cell proliferation in LNPC. (A) shows cellular proliferation when stimulating each naive T cells of PD-1 −/−mice and wt mice. (B) shows the effect of anti-PD-L1 antibody on cellular proliferation in the co-culture of T cells that has already been activated and derived from PD-1 −/−mice or wt mice and LNPC.

Figure 12:
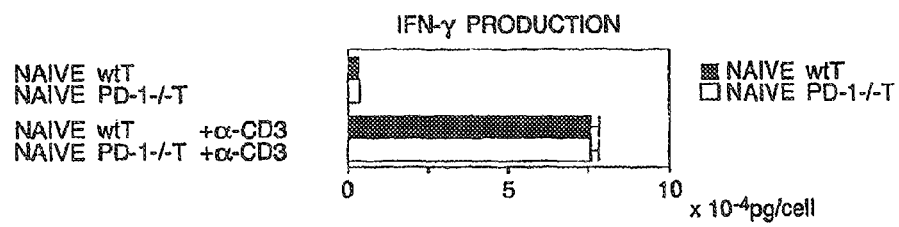
Figure 12:
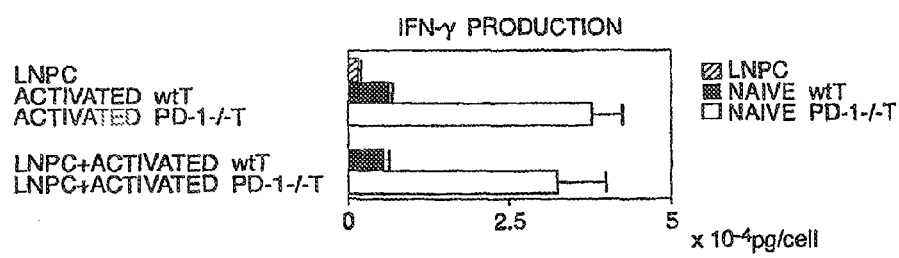
Figure 12:
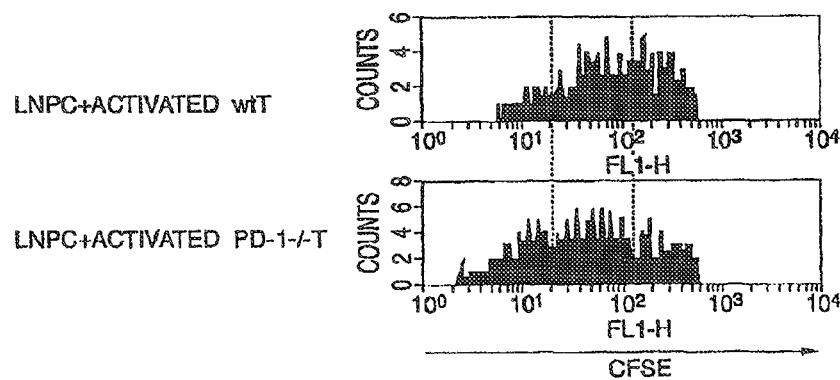

FIG. 12 shows the effect of PD-L1 on cytokine production in LNPC. (A) shows cytokine production when stimulating each naive T cell of PD-1 −/−mice and wt mice. (B) shows the effect of anti-PD-L1 antibody on cytokine production in the co-culture of T cells that has already been activated and derived from PD-1 −/−mice or wt mice and LNPC. (C) shows cell division of the activated T cells from PD-1 −/−mice or wt mice in the co-culture with LNPC.

Figure 13:
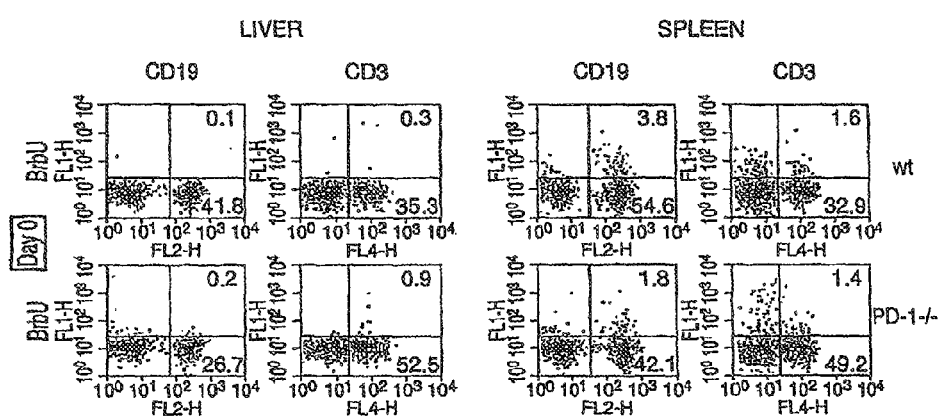
Figure 13:
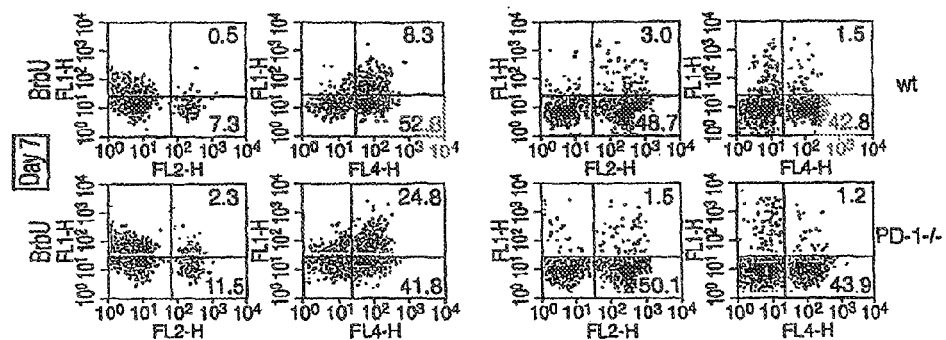

FIG. 13 shows the involvement of PD-1 in T lymphocytes proliferation in virus infected mouse liver. Cellular proliferation of CD19- and CD3-positive lymphoid cells in liver and spleen of PD-1 −/−mice or wt mice on (A) day 0 and (B) day 7 after adenovirus infection are shown.

Figure 14:
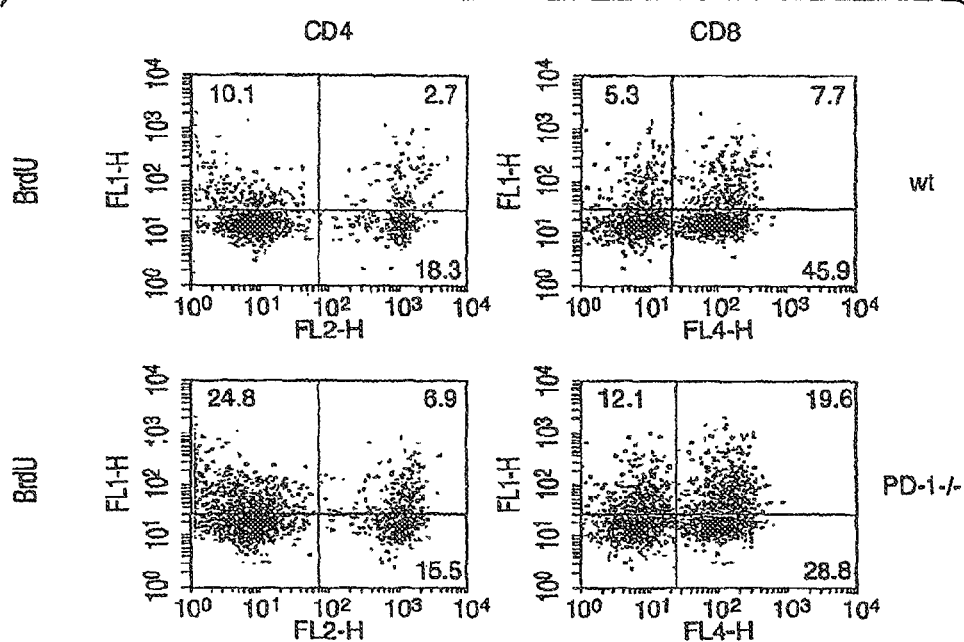
Figure 14:
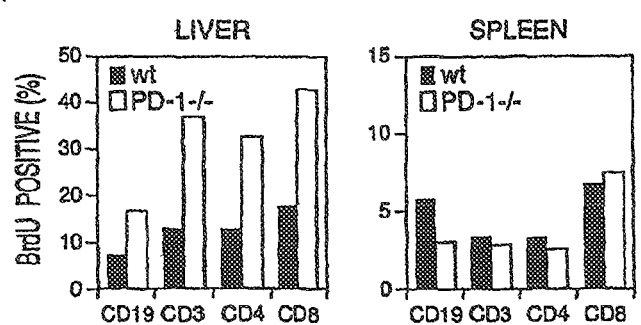

FIG. 14 shows the involvement of PD-1 to cellular proliferation of T lymphocytes in virus infected mouse liver, (A) shows cellular proliferation of CD4- and CD8-posiiive lymphoid cells in liver of PD-1 −/−mice or wt mice on day 7 after adenovirus infection. (B) shows the ratio of various proliferative lymphocytes on day 7 after the infection.

Figure 15:
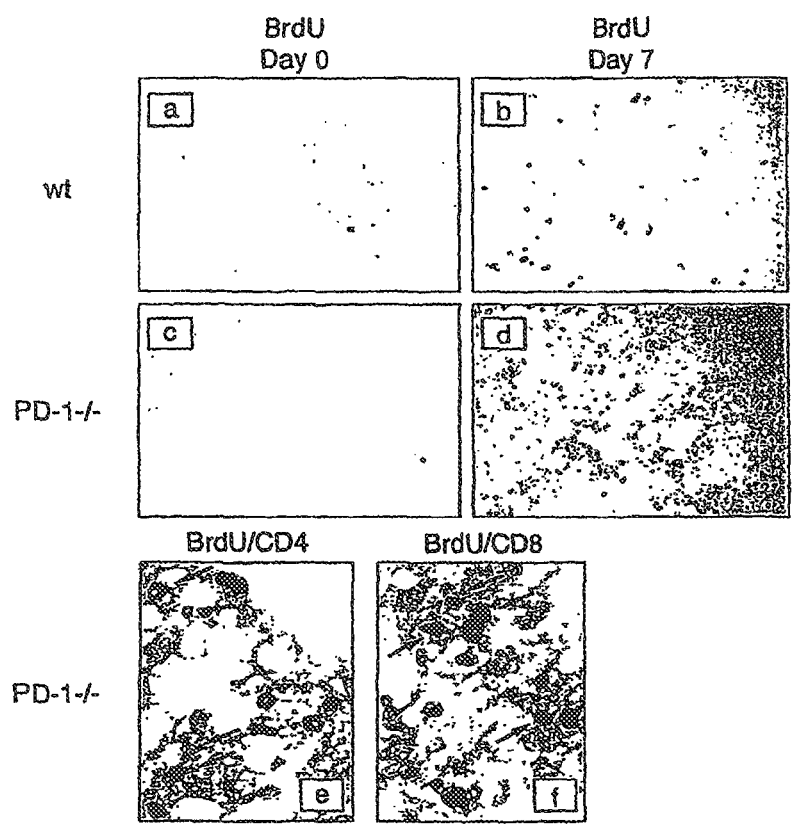

FIG. 15 shows the involvement of PD-1 in virus infection. In this figure, (a)-(d) show tissue staining images that presents each cellular proliferation, in liver of PD-1−/−mice and wt mice on day 0 and day 7 after adenovirus infection, (e) and (f) show cellular proliferation of CD4- and CD8-positive T cells in PD-1 −/−mice on day 7 after adenovirus infection.

Figure 16:
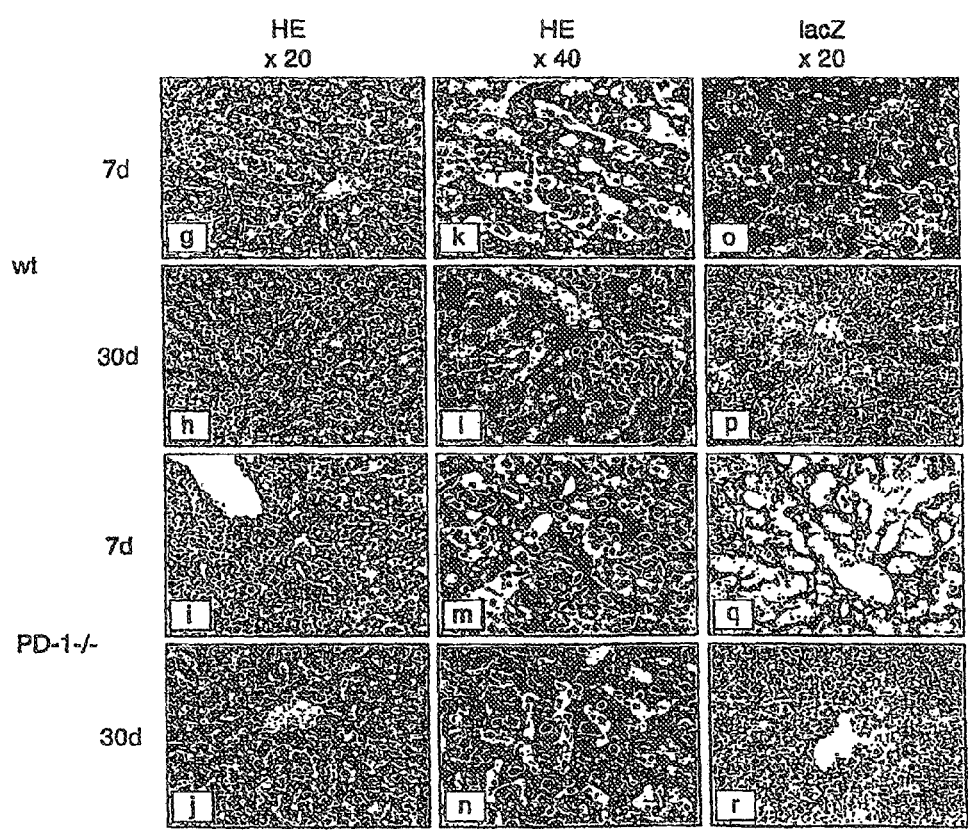

FIG. 16 shows the involvement of PD-1 to virus infection. In this figure, (g)-(n) show hematoxylin & eosin tissue staining images in liver of PD-1 −/−mice and wt mice on day 0 and day 7 after adenovirus infection, (o)-(r) show X-gal tissue staining images in liver of PD-1 −/−mice and wt mice on day 0 and day 7 after adenovirus infection.

Figure 17:
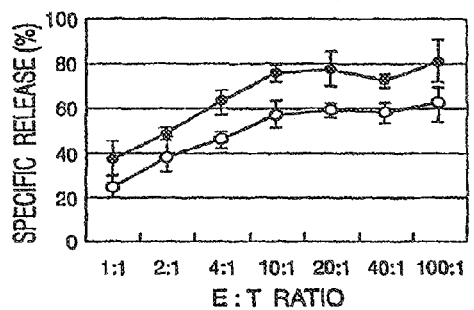
Figure 17:
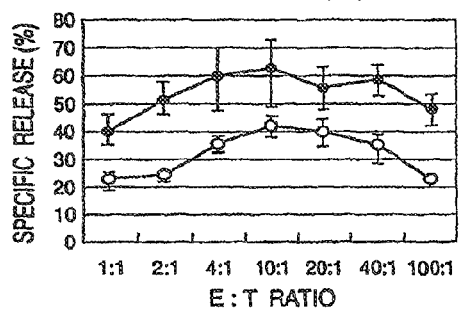
Figure 17:
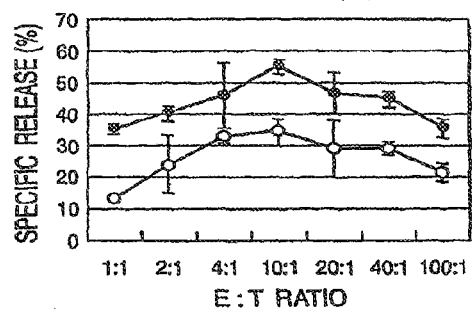
Figure 17:
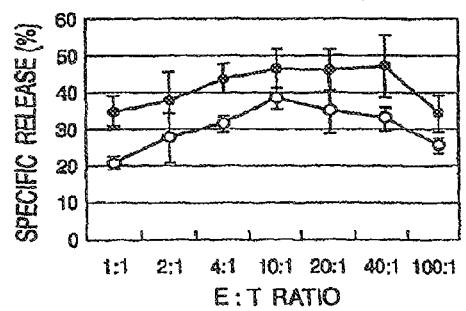

FIG. 17 shows the enhancement of each material to cytotoxic activity. In this figure, (a) the enhancement of anti-mouse PD-1 antibody, (b) the enhancement of anti-mouse PD-L1 antibody, (c) the enhancement of mouse PD-1 Fc, and (d) the enhancement of human PD-1 Fc are shown.

BEST MODE FOR CARRYING OUT INVENTION

The following example explains the present invention more concretely, but do not limit the range of the present invention.

Example 1

A mouse PD-L1 expression vector was constructed by being inserted and ligated mouse PD-L1 cDNA (Journal of Experimental Medicine (2000), vol. 19, issue 7, p. 1027-1034) digested with restriction enzyme EcoRI to pApuroXS expression vector (*The EMBO Journal* (1994), vol. 13, issue 6, p. 1341-1349), The expression vector pApuroXS-PD-L1 was transacted into P815 cells by electroporation (360V, 500 μF). The P815 cells were cultured in RPMI-1640 medium including FCS (10%), 2-mercaptoethanol ($10^{-5}$ M), and various antibiotics. The P815 cell lines which stably expressed mouse PD-L1 can be cloned by subculturing as resistant cells under medium including antibiotic puromycin (3 μg/ml). PD-L1 expression can be confirmed by flow cytometric analysis. FIG. 1(A) shows flow cytometries presenting (i) PD-1expression of H-2L$^d$-specific 2C CTL clones and (ii) PD-L1 expression in PD-L1expressing stable transformant of P815 (cell line derived from mastocytoma). Transformed B16 cell lines (B16/PD-L1) stably expressing PD-L1 were cloned by a similar method (FIG. 1(A) (iii)-(v)) pEFBOSneo-PD-L1 (Nucleic Acid Research (1990), vol. 18, issue 17, p. 5322) constructed as a expression vector by a similar method was used, and G418 (0.5 mg/ml) was used for selective culture of the cell lines.

cDNA coding protein to connect tandem 6xhis peptide tag (His-Tag) to 3' end side of total length mouse PD-L1 cDNA was inserted in expression vector pVL1393(the trade name:

purchase from Clonetech) after being digested by restriction enzyme EcoRI and NotI. Then, this expression vector was continuously introduced to SF9insect cells (purchased from Invitrogen), and the inclusion body was collected. This inclusion body virus was infected to HiFive insect cells (purchased from Invitrogen) by culturing for 2 days at 27° C. The purified PD-L1 protein that are used as antigen was obtained by processing cell lysate dissolved with buffer solution (Tris-HCl (50 mM, pH7, and 1% TritonX-100), EDTA (10 mM), and NaCl (150 mM), various protease inhibitors) with Ni-sepharose column chromatography.

The dialyzed PD-L1 protein was immunized to female wister rat at 8 weeks age (purchased from SLC Japan) with a complete Freund adjuvant (purchased from Amersham) and after several days, $2\times10^8$ of cells collected from peripheral lymph node were fused with the same number of SP2/0 cells using PEG1500. Further, the fused cells were selected by cultuting in RPMI1640 medium (HAT (purchased from Sigma), Origen (10%, purchased from Igen), and FCS (10%), 2-mercaptoethanol ($10^{-5}$M), and various antibiotics), and the presence of the antibody production was confirmed by flow cytometric analysis. The monoclonal antibody (1-111) to PD-L1 was obtained by purification of the collected peritoneal fluid with protein G sepharose column chromatography after transfering the established hybridoma (hybridomas recognized with International Trust Number: FERM BP-8396) to Balb/C nu/nu mice. As antibodies used by flow cytometry, etc., biotinated antibodies using Sulfo-NHS-LC-biotin (the trade name: purchased from Pierce) can be used.

Further, anti-human PD-1 antibody (the monoclonal antibody producted from hybridomas recognized with International Trust Number: FERM BP-8392) was prepared according to a similar method.

Cytotoxicity assay was executed by $^{51}$Cr (chromium) separation assay.

Figure 1:
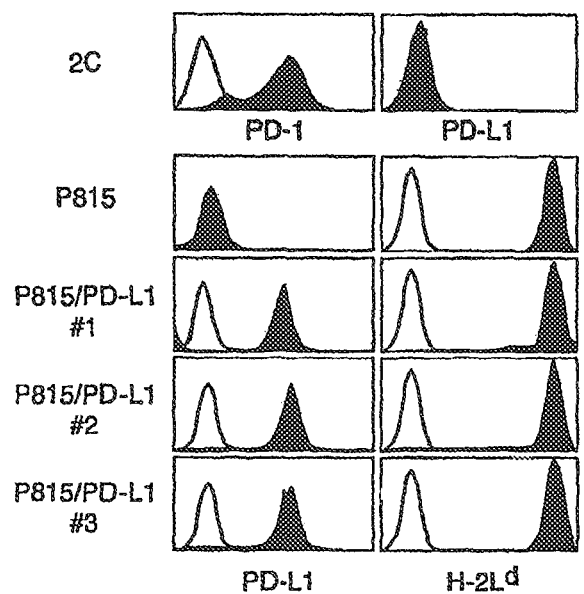
Figure 1:
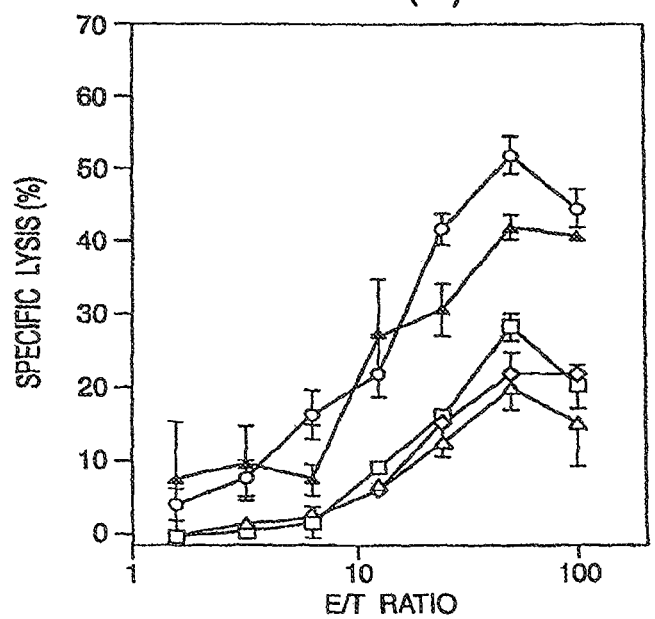

2C cells (*Journal of Immunology* (1996), vol. 157, issue 2, p. 670-678) are $(H-2L)^d$ alloreactive cytotoxic T-cells derived from 2C transgenic B6 mice. After mixing 2C cells (E: effector) together with $^{51}$Cr-labeled P815 cells (T; target) (circle), three kinds of PD-L1-expressing P815 cells (P815/PD-L1) (square, diamond, and triangle) respectively, or further under the presence of 10 mg/ml rat anti-PD-L1 F(ab')$_2$ IgG (filled triangle), a result of measuring separated $^{51}$Cr for 4 hours with various E/T ratio is shown in FIG. 1 (B).

Anti-PD-L1 antibody (anti-PD-L1 F(ab')$_2$) recovered the decreased cytotoxic activity of cytotoxic T lymphocytes. Those results suggested that inhibition of PD-1 and PD-L1 signal by inhibiting PD-L1 function could reinforce cytotoxic activity to carcinoma cells.

Example 2

The tumor growth and the survival rate of mice was evaluated by hypodermicaliy transfering $1\times10^6$ of P815 cells (n=6) or P815/PD-L1 cells (n=6) to syngeneic DBA/2 mice respectively. The result is shown in FIG. 2 (A). In this figure, circles show P815 cell lines transplanted group, and squares and triangles show PD-L1-expressing P815 cell lines transplanted group respectively. Further, histological analysis of P815/PD-L1 cells transferred group was executed. FIG. 2(B) shows staining images dyed with hematoxylin & eosin after being fixed by 10% formaldehyde and embedded into paraffin. In this figure, a shows a view (×40) that presents invasion of tumor cells across the abdominal wall and the peritoneum, b shows the same view (×400), c shows the view of invasion into spleen, and d shows the view of invasion into liver.

In the P815 cells transplanted group, P815 cells proliferation was suppressed and 30 percent of mice in this group lived by 6-7 weeks, while in PD-L1-expressing P815 cells (P815/PD-L1) transplanted group, carcinoma cells proliferation was remarkable and all mice died by 2-4 weeks (FIG. 2(A)). P815/PD-L1 cells were observed to permeate across the peritoneal cavity and the abdominal cavity, and further those metastases to liver and spleen (FIG. 2(B) a-d).

Example 3

After co-culturing $2\times10^6$ of 2C cells togather with $5\times10^6$ of P815 cells or P815/PD-L1 cells only, or P815/PD-L1 cells under the presence of 10 mg/ml rat anti-PD-L1 F(ab')$_2$ IgG respectively, IFN-y in culture supernatant at 24 hours was measured with ELISA kit (purchased from Bioscience). The result is shown in FIG. 3 (A).

FIG. 3 (B) shows the result of evaluating of the tumor growth and the survival rate of mice of which anti-rat IgG (square) or anti-PD-L1 F(ab')$_2$ IgG (0.1 mg/mouse) (circle) was intraperitoneally administered to syngeneic DBA/2 mice (n=10) to which $3\times10^6$ of P815/PD-L1 cells had been hypodermically transferred on day 1, 3, 5, and 7 after the cell-transfer.

Anti-PD-L1 antibody restored IFN-y production from cytotoxic T lymphocytes which had been suppressed by P815/PD-L1 (FIG. 3(A)). Administration of anti-PD-L1 antibody suppressed carcinoma cell growth, and showed the clear survival effect (FIG. 3(B)). This result presents that administration of anti-PD-L1 antibody is effective on cancer treatment.

Example 4

$1\times10^6$ of B16 melanomas (n=6) or B16/PD-L1 cells (n=6) were hypodermically transferred to B6 mice (n=6) respectively, and the same number of B16/PD-L1 cells were transferred to PD-1 transgenic B6 mice (n=5) and PD-1 gene homo-deficient B6 mice (PD-1/-(n=4)) (*Science*(2001), vol. 291, issue 5502, p. 319-332), each tumor growth was measured by 25 days thereafter. FIG. 4 shows the result.

Example 5

Tumor growth of which (n=9) anti-rat IgG or anti-PD-L1 F(ab')$_2$ IgG (0.1 mg/mouse) was intraperitoneally administered to syngeneic Balb/C mice to which $2.5\times10^8$ of J558 myeloma cells had been hypodermically transferred on day 3, 5, and 7 after the cell-transfer was evaluated. Each tumor growth in PD-1 gene homo-deficient Balb/C mice and Balb/C mice (n=4) to which J558 myeloma cells had been hypodermically transferred were compared (FIG. 5(B)).

Administration of anti-PD-L1 antibody suppressed PD-L1-expressing J558 carcinoma cells proliferation (flow cytometries of PD-L1 expression in various myeloma cell lines are shown in FIG. 5(A)) (FIG. 5(B)). The transplanted tumor cells proliferation was completely inhibited in PD-1-deficient mice to which J558 cells had been transplanted (FIG. 5(*c*)). These results present that inhibition of PD-L1 or PD-1 is effective on cancer treatment.

Example 6

Vascular endothelial cells (hereafter, abbreviated as ECs) was gathered from mouse heart by the method of Marelli-Berg (*Journal of immunological methods* (2000), vol. 244, issue 1-2, p. 205-215). Concretely, heart tissue digested by collagenase was pre-cultured followed by being pre-cultured with mouse Ig and co-cultured together with FITC-modified anti-CD3 antibody, the same modified anti-CD105 antibody, the same modified anti-isolectin B4 antibody, and anti-FITC bead. These vascular endothelial cells were purified by positive selection using Magnetic-activated cell-sorting separation columns (the trade name; purchased from Miltenyi Biotec).

PD-L1 and PD-L2 expressions in the gathered vascular endothelial cells were confirmed by flow cytometry. The cell labelling was executed using anti-PD-L1 antibody (the antibody name; 1-111), anti-PD-L2 antibody (the antibody name: #122), and fluorescent labelling second antibody (FIG. 6(A)). The analysis was executed 10,000 events with Facscalibur (the equipment name: purchased from Becton Dickinson) using CellQuest software (purchased from Dickinson). PD-L1 or PD-L2 expression is shown as shedding curve, and control Ig is shown as filling curve.

PD-L1 expression in each mouse tissue was confirmed by tissue staining. Before 1 hour each tissue sampling, 100 μl of PBS which 100 μg of biotin-labelling anti-PD-L1 antibody (1-111) had been dissolved was intravenously administered to mouse. Then, 5 μm frozen section was fixed by 4% paraformaldehyde (PFA), and dyed with Streptavidin-FITC. Each section was countered staining by Phalloidin (FIG. 6(B) shows PD-L1 expression in (a) eyeball, (b) submaxillary gland, (c) heart, (d) lung, (e) liver, (f) kidney. In this figure, Ch presents choroid, CV presents vena centralis, GI presents glomerule, and Re presents retina. Each arrow presents vascular endothelial cells. Each staining figure is 40× enlargement view.). PD-L1 expression was observed in capillary endothelium of heart, lung, kidney, stomach, small intestine, submandibular gland, eyeball, and liver. The expression in liver was localized in liver sinusoidal capillary.

Example 7

PD-L1 expression in liver non-parenchymal cells (hereafter, abbreviated with LNPCs) was confirmed by tissue staining (FIG. 7(A)) and flow cytometry (FIG. 7(B)). In the tissue staining, 5 μm liver frozen section fixed with 3% of PFA was preprocessed by rat serum followed by being reacted for 1 hour at room temperature using biotin-labeled anti-PD-L1 antibody (1-111) or biotin-labeled anti-ICAM-1 antibody (the trade name: purchased from BD Pharmingen), and then the biotin antibodies were visualized by tyramide signal amplification (TSA) fluorescence system (the equipment name: purchased from PerkinElmer Life Sciences) (FIG. 7(A) shows ICAM-1 expression, FIG. 7(B) shows PD-L1 expression, and CV presents vena centralis. Each staining figure is 40× enlargement view.).

LNPCs were isolated from mouse liver according to the pronaseE method (*Experimental Cell Research* (1976, vol. 99, p. 444-449). Concretely, LNPCs obtained by which liver is circulated with pronaseE solution (Merck) were cultured and were separated by density gradient centrifugation. Relative distribution of Kupffer cells (CD54+, CD11bhigh) in the cell suspension is 20-25%, and that of liver perisinusoidal space endothelial cells (hereafter, abbreviated with LSECs.) (CD54+, CD11bhigh) is 75-80% Kupffer cells and LSECs were doubly stained using FITC-labeled anti-CD11b antibody, each biotinated monoclonal antibody to ICAM-1, PD-L1, B7-1, and B7-2, and PE-labeled Streptavidin, respectively. Kupffer cells and LSECs were gate as CD11b high and CD11b low cell, respectively (FIG. 8).

PD-L1 expressed together with ICAM-1, B7-1, and B7-2 in Kupffer cells, while the expression was weak in LSECs (FIG. 8).

Example 8

Native T cells were refined (refining degree 90% or more) from spleen and lymphoid of PD-1 gene homo-deficient mice (PD-1 −/−) or wild type C57BL/6 mice (wt) by a negative selection using T-cell enrichment column (the trade name; purchased from Genzyme). The cells cultured for 48 hours with 10 μg/ml of anti-CD3 monoclonal antibody (2C11) were activated. The naive T celts activated by the above method were doubly stained using FITC-labeled anti-CD4 antibody or APC-labeled anti-CD8 antibody, PE-labeled anti-CD25 antibody, PE-labeled anti-CD4 antibody, PE-labeled anti-CD69 antibody, or PE-labeled anti-CTLA-4 antibody, biotin-labeled anti-B7-1 (CD80) antibody or biotin-labeled anti-B7-2 (CD86) antibody, and anti-PD-1 antibody (the antibody name: J43, monoclonal antibody producted from hybridomas recognized by International Trust Number FERM BP-8118) or anti-PD-L1 antibody (1-111), and each molecule expressions were analyzed by flow cytometry (FIGS. 9 and 10).

The hybridomas identified by International Trust Number FERM BP-8118 had been deposited as Trust Number FERM P-18356 to National Institute of Advanced Industrial Science and Technology, International Patent Organism Depositary in Central 6, 1-1-1 Higashi, Tsukuba, Ibaraki, Japan (ZIP code 305-8566) at May 30, 2001, and was transferred to International Deposit at Jul. 16, 2002.

Example 9

The naive T cells activation of PD-1 gene homo-deficient mice (PD-1 −/−) or wild type mice (wt) was executed by the method described in example 8. Proliferation of these activated cells was measured by BrdU incorporation method (FIG. 11(A)). The proliferation was measured by adding BrdU at the last 6 hours of 48 hours to label the cells and measuring using Proliferation ELISA kit (the trade name: Purchased from Roche). The amount of IFN-γ production at this time was measured in ELISA Kit (the trade name: purchased from Genzyme) (FIG. 12(A)).

T cells derived from PD-1 gene homo-deficient mice (PD-1 −/−) or wild type mice (wt) was beforehand activated by the method described in example 8. The activated T cells were respectively cultured for 60 hours under the presence or the absence of Mitomycin C-processed LNPCs of wild type mice and under the presence or the absence of 30 μg/ml of anti-PD-L1 antibody (1-111) (rat IgG as control) and 20 μg/ml of CTLA4-Ig (Genzyme) (human IgG as control), and the cells proliferation for the last 12 hours was measured by BrdU incorporation method (FIG. 11(B)). Further, the amount of IFN-γ production at 48 hours was measured (FIG. 12(B)).

As to the amount of IFN-γ production when naive T cells were activated, a significant difference between PD-1 −/− and wild type mice was not observed. On the other hand, in the activated T cells, the amount of IFN-γ production of T cells derived from wild type mice was significantly lower than that derived from PD-1 −/− (FIG. 12). Therefore, it was suggested that the effect of PD-1 inhibitory action on the activated T cells could be higher than the effect on naive T cells activation.

In co-culture of the activated T cells derived from wild type mice and LNPCs, a significant difference in the cellular proliferation and the amount of IFN-γ production of these T cells was not observed, while in the co-culture of the activated T cells derived from PD-1 −/−mice and LNPCs, a significant increase in the cellular proliferation of these T cells was observed (FIG. 11(B), FIG. 12(B)). In adding anti-PD-L1 antibody to the co-culture of the activated T cells derived from wild type mice and LNPCs, an increase in the cellular proliferation of these T cells was observed (FIG. 11(B)). These results suggest that PD-1 or PD-L1 of LNPCs could take part in suppression of T cells activation and lack of PD-1 or inhibition of interaction between PD-1 and PD-L1 could activate T cells.

The activated T cells of PD-1 gene homo-deficient mice (PD-1 −/−) or wild type mice (wt) was labeled by 5 μM CFSE (5-(6)-carboxy-fluorescein diacetate succinimidyl diester) (the trade name: purchased from Molecular probes) and was co-cultured together with LNPCs for 48 hours. Cell division at this time was decided by CFSE activity measurement using FACS (FIG. 12(C)).

It was suggested that the cellular proliferation suppression of the activation T cells could cause in cytostasis suppression and PD-1 signal could suppress cell division of T cells (FIG. 12(C)).

Example 10

PD-1 gene homo-deficient mice (PD-1−/−) or wild type mice (wt) (3 per a group) were infected in adenoviruses by intravenous administration of $10^9$-$10^{10}$ PFU (plaque-(plaque-forming units) of Ad-lacZ. Ad-lacZ used here, which are 5 type adenovirus with lacZ gene, lacks E1 and E 3 region and can be purified by cesium chloride density-gradient centrifugation (*Nucleic Acid Research* (1995), vol. 234, issue 19, p. 3816-3821) after proliferating them in 293 cells. On day 0 or 7 after infection, spleen cells and intrahepatic lymphocytes that had been gathered after intravenous administration of 0.5 mg of BrdU (the trade name: purchased from Sigma) to the mice at 1 hour before slaughtering were doubly labeled by anti-BrdU antibody and anti-CD19 antibody, or anti-CD3 antibody (FIG. 13).

The cells on day 7 after infection were doubly labeled by anti-BrdU antibody, anti-GD19 antibody, anti-CD3 antibody, anti-CD4 antibody, and anti-CD8 antibody (FIG. 14(B), each bar graph shows the ratio of BrdU-positive cells).

In adenovirus infected PD-1−/−mice liver, the ratio of each proliferative (BrdU positive) lymphocyte (CD19 positive, CD3 positive, CD4 positive, or CD8 positive) had increased compared to that in similarly infected wild type mice liver. On the other hand, since such a phenomenon in spleen was not observed, it was suggested that PD-1 could inhibit T cells proliferation in inflammatory tissues (FIG. 14(B)).

Example 11

On day 0 or 7 after $10^9$-$10^{10}$ PFU of Ad-lacZ had been intravenously administered to PD-1 gene homo-deficient mice (PD-1−/−) or wild type mice (wt) (3 per a group), liver slices that had been gathered after intravenous administration of 0.5 mg of BrdU (the trade name: purchased from Sigma) to the mice at 1 hour before slaughtering were doubly labeled by anti-BrdU antibody (FIG. 15(a)-(d), 20× enlargement view). Liver slices of PD-1 gene homo-deficient mice (PD-1−/−) on day 7 after infection were doubly labeled by anti-BrdU antibody, anti-CD19 antibody, anti-CD3 antibody, anti-CD4 antibody, and anti-CD8 antibody (FIG. 15(e), (f), 40× enlargement view.).

In wild type mice liver on day 30 after infection, the locally and medium cell invasion to sinusoidal capillary and non-parenchymal region was observed, but in PD-1−/− mice, hepatitis symptom was not observed (FIG. 16(h), (i) and (j), (n)).

Liver slices of PD-1 gene homo-deficient mice (PD-1−/−) or wild type mice (wt) on day 7 or 30 after infection were stained by hematoxylin & eosin (FIG. 16(g)-(j), 20× enlargement view, (k)-(n), 40× enlargement view,) and X-gal (FIG. 16 (o)-(r), 40× enlargement view). These results presented that PD-1 signal could take part in the exclusion of viruses by which the proliferation of effector T calls in virus infected tissue could be induced.

Example 12

P-815/PD-L1 cells compellingly expressing mouse PD-L1 were sown into culture flask and were cultured in usual medium including 5 μg/mL of puromycin (purchased from Sigma) (hereafter, abbreviated as selective medium) at 37° C. under 5% $CO_2$/95% air until to be 50%-90% confluent. Mouse cytotoxic T lymphocyte 2C cells were subcultured for several days in usual medium together with P-815 cells processed by MMC (Mitomycin C) and culture supernatant of ConA-stimulated rat splenic cells. The collected P-815/PD-L1 cells were cultured for 15 minutes after adding 3 μL of BATDA Reagent of DELFIA EuTDA Cytotoxicity Reagents (purchased from PerkinElmer). Then, they were washed with PBS. 2C cells subcultured for 5-8 days after adding P-815 cells were used.

As subject substrates, 20 μL (10 ng/mL) of anti-mouse PD-1 antibody (FIG. 17, anti-mPD-1Ab (J43)), anti-mouse PD-L1 antibody (anti-mPD-L1Ab(1-111) in this figure), mouse PD-1 Fc (mPD-1Fc in this figure), human PD-1 Fc (hPD-1Fc in this figure), mouse IgG2aκ(Control Ig in this figure), or PBS were dispensed into 96 well plate, and then 50μL of P-815/PD-L1 cells or usual medium ware added. Further, 50 μL of 2 C cells, usual medium, or usual medium including 1% Triton×100 were added. 50 μL of supernatants in wells which the usual medium were added were collected for background and other supernatants were preserved at 37° C. until being collected. The residual cells were cultured for 4 hours. The 96 well plates were centrifuged and the supernatants were collected, 200 μL of DELFIA Europium Solution of Cytotoxicity Reagents (purchased from Perkin Elmer) were added to the collected supernatants, and were shaken for 15 minutes. After shaking, time resolved fluorescence measurement was executed with ARVOsx multi-label counter (VVALLAC). The supernatants in wells that the usual medium including 1% Triton×100 was added were used as a high control, and the one in wells that the usual medium were used as a low control.

The evaluated group is composed of a subject substrate, P-815/PD-L1 cells, and 2C cells, the high control group is composed of PBS, P-815/PD-L1 cells, and usual medium including 1% Triton×100, and the low control group is composed of PBS, P-815/PD-L1 cells, and usual medium, the 2C cell control group is composed of PBS, usual medium, and 2C cells, and the background group is composed of PBS, P-815/PD-L1 cells, and usual medium, CTL activity (%) was calculated by the following formula. All values are the one that had been subtracted by the average of the background.

CTL activity (%)=([the measurement of the evaluation group]−[the measurement of the 2C cell control group]−[the measurement of the low control group])/([the measurement of the high control group][the measurement of the low control group])×100

Anti-PD-1 antibody, anti-PD-L1 antibody, and PD-1 Fc have significantly reinforced-CTL activity (FIG. 17 (a)-(d), E: T ratio presents the mixing ratio of 2C cells and PD-L1/P815 cells).

Example 13

The inhibiting effect of anti-PD-1 antibody on cancer metastasis was evaluated by intraperitoneal administration of anti-mouse PD-1 monoclonal antibody to C57BL/6 mice to which B16 melanoma cells had been transferred at intervals of 2 days followed by measuring the liver weight on day 18 after transfer.

The increase in the liver weight of anti-PD-1 antibody administrated group was significantly suppressed than that in control IgG administrated control group (liver weight/carcinoma cell non-transferred group: 1.3 g, decrease from control group: 6.8 g to anti-PD-1 antibody administrated group: 3.5 g.). The suppression of the increase in this weight presents that the metastasis of B16 melanoma cells is suppressed.

The invention claimed is:

1. A method of treating a metastatic melanoma comprising intravenously administering an effective amount of a composition comprising a human or humanized anti-PD-1 monoclonal antibody and a solubilizer in a solution to a human with the metastatic melanoma, wherein the administration of the composition treats the metastatic melanoma in the human.

2. The method of claim 1, wherein the solubilizer comprises polysorbate 80.

3. The method of claim 1, wherein the composition further comprises an excipient.

4. The method of claim 1, further comprising administering an anticancer agent to the human.

5. The method of claim 4, wherein the anticancer agent is a chemotherapy drug.

6. The method of claim 5, wherein the chemotherapy drug is selected from an alkylating agent, a nitrosourea agent, an antimetabolite, an antitumor antibiotic, an alkaloid derived from a plant, a topoisomerase inhibitor, a hormone therapy medicine, a hormone antagonist, an aromatase inhibitor, a P-glycoprotein inhibitor and a platinum complex derivative.

7. The method of claim 4, wherein the anticancer agent is an anti-CTLA-4 antibody.

8. The method of claim 1, wherein the anti-PD-1 monoclonal antibody is a humanized antibody.

9. The method of claim 1, wherein the anti-PD-1 monoclonal antibody is a human antibody.

10. The method of claim 4, wherein the anti-PD-1 monoclonal antibody is a humanized antibody.

11. The method of claim 4, wherein the anti-PD-1 monoclonal antibody is a human antibody.

12. The method of claim 7, wherein the anti-PD-1 monoclonal antibody is a humanized antibody.

13. The method of claim 7, wherein the anti-PD-1 monoclonal antibody is a human antibody.

14. The method of claim 1, wherein the metastatic melanoma expresses PD-L1.

15. The method of claim 1, wherein the metastatic melanoma expresses PD-L2.

16. The method of claim 4, wherein the metastatic melanoma expresses PD-L1.

17. The method of claim 4, wherein the metastatic melanoma expresses PD-L2.

18. The method of claim 7, wherein the metastatic melanoma expresses PD-L1 or PD-L2.

19. The method of claim 8, wherein the metastatic melanoma expresses PD-L16.

20. The method of claim 8, wherein the metastatic melanoma expresses PD-L2.

21. The method of claim 9, wherein the metastatic melanoma expresses PD-L1.

22. The method of claim 9, wherein the metastatic melanoma expresses PD-L2.

23. The method of claim 10, wherein the metastatic melanoma expresses PD-L1 or PD-L2.

24. The method of claim 11, wherein the metastatic melanoma expresses PD-L1 or PD-L2.

25. The method of claim 14, wherein the PD-L1 expression is identified by immunohistochemistry.

26. The method of claim 15, wherein the PD-L2 expression is identified by immunohistochemistry.

27. The method of claim 16, wherein the PD-L1 expression is identified by immunohistochemistry.

28. The method of claim 17, wherein the PD-L2 expression is identified by immunohistochemistry.

29. The method of claim 18, wherein the PD-L1 or PD-L2 expression is identified by immunohistochemistry.

30. The method of claim 23, wherein the PD-L1 or PD-L2 expression is identified by immunohistochemistry.

* * * * *

UNITED STATES PATENT AND TRADEMARK OFFICE
CERTIFICATE OF CORRECTION

PATENT NO. : 9,073,994 B2
APPLICATION NO. : 14/550585
DATED : July 7, 2015
INVENTOR(S) : Honjo et al.

It is certified that error appears in the above-identified patent and that said Letters Patent is hereby corrected as shown below:

In the Claims:

Claim 19:

Column 26, line 22, replace "PD-L16" with "PD-L1"

Signed and Sealed this
Third Day of November, 2015

Michelle K. Lee
*Director of the United States Patent and Trademark Office*